US008673573B2

(12) United States Patent  
Lee et al.

(10) Patent No.: US 8,673,573 B2  
(45) Date of Patent: Mar. 18, 2014

(54) USE OF EIF3M FOR THE DIAGNOSIS AND TREATMENT OF CANCER

(75) Inventors: Yeon-Su Lee, Goyang-si (KR); Sung-Ho Goh, Goyang-si (KR); Sung-Hye Hong, Seoul (KR); In-Hoo Kim, Goyang-si (KR); Jin-Sook Jeong, Busan (KR)

(73) Assignee: National Cancer Center, Goyang-Si (KR)

( * ) Notice: Subject to any disclaimer, the term of this patent is extended or adjusted under 35 U.S.C. 154(b) by 0 days.

(21) Appl. No.: 12/997,560

(22) PCT Filed: Oct. 7, 2010

(86) PCT No.: PCT/KR2010/006878  
§ 371 (c)(1),  
(2), (4) Date: Sep. 23, 2011

(87) PCT Pub. No.: WO2011/052906  
PCT Pub. Date: May 5, 2011

(65) Prior Publication Data  
US 2012/0201837 A1 Aug. 9, 2012

(30) Foreign Application Priority Data  
Oct. 29, 2009 (KR) .................. 10-2009-0103723

(51) Int. Cl.  
*A61K 31/713* (2006.01)  
*C12Q 1/68* (2006.01)

(52) U.S. Cl.  
USPC ........................................ 435/6.14; 435/6.12

(58) Field of Classification Search  
None  
See application file for complete search history.

(56) References Cited

U.S. PATENT DOCUMENTS 5,242,813 A 9/1993 Pastan et al. ............... 435/70.21  
2010/0184125 A1* 7/2010 Huang et al. ................. 435/40.5

FOREIGN PATENT DOCUMENTS

WO WO 2011/052906 5/2011

OTHER PUBLICATIONS

Chew et al., Genome-wide silencing in *Drosophila* captures conserved apoptotic effectors, Jul. 2, 2009, Nature, vol. 460, p. 123-127.*

Mettlin, et al., Relative sensitivity and specificity of serum prostate specific antegen (PSA) level compared with age-referenced PSA, PSA densitiy, and PSA change, 1994, Cancer, vol. 74, No. 5, p. 1615-1620.*  
Ludwig, et al., Biomarkers in cancer staging, prognosis and treatment selection, 2005, Nature Reviews: Cancer, vol. 5, p. 845-856.*  
Brawer, et al., Measurement of complexed PSA improves specificity for early detection of prostate cancer, 1998, Urology, vol. 52, p. 372-378.*  
Budman et al., Biomarkers for detection and surveillance of bladder cancer, 2008, CUAJ, vol. 2, No. 3, p. 212-221.*  
Sian Jones, et al., Core signaling pathways in human pacreatic cancer revealed by global genomic analyses, 2008, Science, vol. 321, p. 1801-1806.*  
Brummelkamp et al., "A System for Stable Expression of Short Interfering RNAs in Mammalian Cells," *Science* 296:550-553, 2002.  
Chien et al., "Novel cationic cardiolipin analogue-based liposome for efficient DNA and small interfering RNA delivery in vitro and in vivo," *Cancer Gene Therapy* 12:321-328, 2005.  
Filleur et al., "SiRNA-mediated Inhibition of Vascular Endothelial Growth Factor Severely Limits Tumor Resistance to Antiangiogenic Thrombospondin-1 and Slows Tumor Vascularization and Growth," *Cancer Research* 63:3919-3922, 2003.  
Gawin et al., "A 7.5 Mb Sequence-Ready PAC Contig and Gene Expression Map of Human Chromosome 11p13-p14.1," *Genome Research* 9:1074-1086, 1999.  
Goh et al., "eIF3m expression influences the regulation of tumorigenesis-related genes in human colon cancer," *Oncogene* 30(4):398-409, 2011. (Abstract Only).  
International Search Report, for International Application No. PCT/KR2010/006878, mailed Jun. 23, 2011, 4 pages.  
NCBI GenBank Database, Accession No. NM_006360, "Home sapiens eukaryotic translation initiation factor 3, subunit M (EIF3M), mRNA," dated Aug. 20, 2006, retrieved from http://www.ncbi.nlm.nih.gov/nuccore/52851442?sat=11&satkey=6051279, 3 pages.  
Office Action, for Korean Application No. 10-2009-0103723, dated Jun. 24, 2011, 5 pages.  
Perez et al., "A New Class of Receptor for Herpes Simplex Virus Has Heptad Repeat Motifs That Are Common to Membrane Fusion Proteins," *Journal of Virology* 79(12):7419-7430, 2005.  
Sui et al., "A DNA vector-based RNAi technology to suppress gene expression in mammalian cells," *Proc. Natl. Acad. Sci. USA* 99(8):5515-5520, 2002.

* cited by examiner

*Primary Examiner* — Hong Sang  
*Assistant Examiner* — Michael D Allen  
(74) *Attorney, Agent, or Firm* — Seed IP Law Group PLLC

(57) ABSTRACT

Disclosed are a cancer marker-detecting composition comprising an agent for measuring an mRNA or protein expression level of eIF3m, a cancer diagnosis kit comprising the same, a method for detecting an eIF3m polynucleotide or protein by treating a biological specimen with the agent to detect a substance binding specifically to the agent and quantitatively comparing the substance between a subject and a normal control, and a method for the treatment and prevention of cancer comprising an agent for down-regulating the expression of an eIF3m polynucleotide or protein.

2 Claims, 14 Drawing Sheets

Fig. 4
a
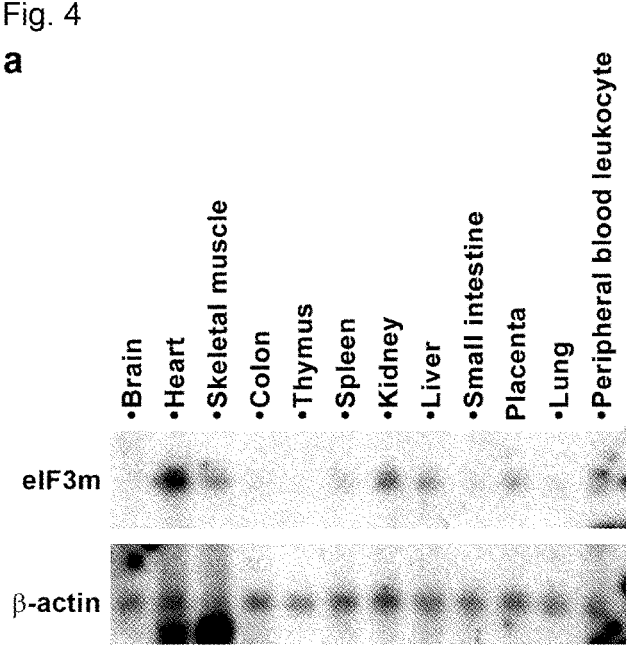
b
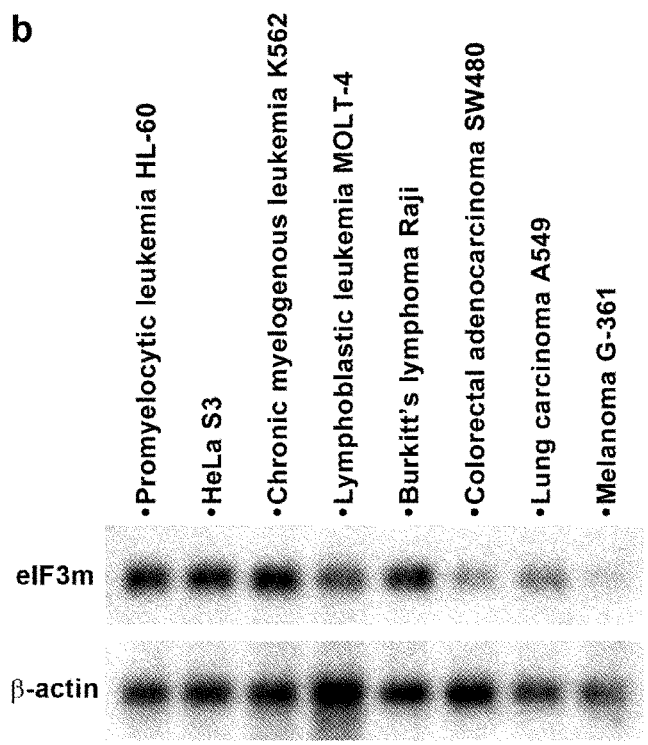

Fig. 7
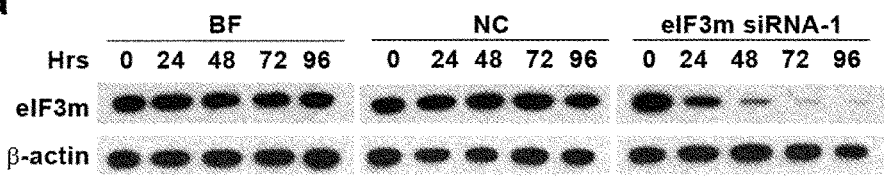
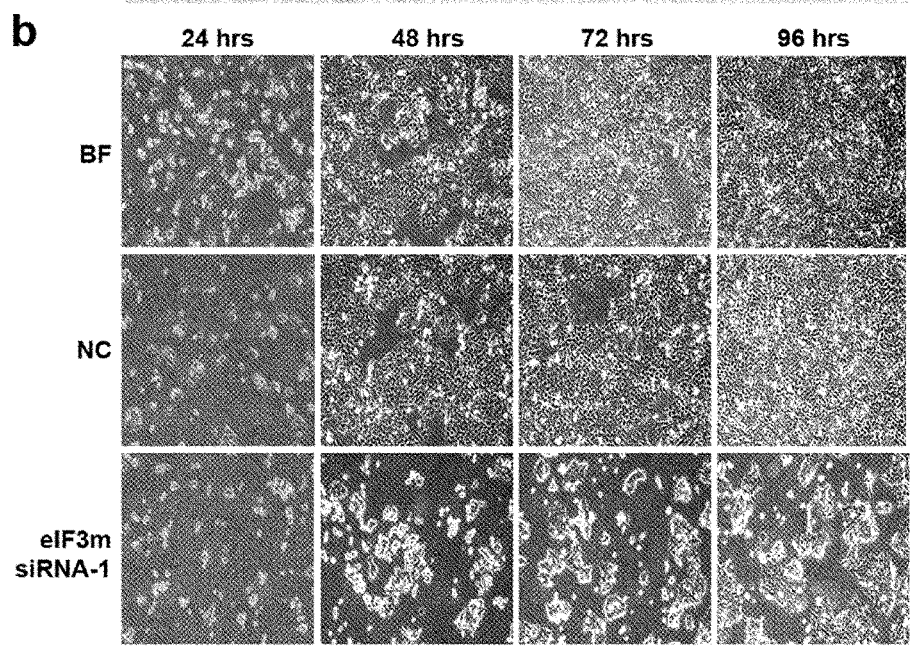
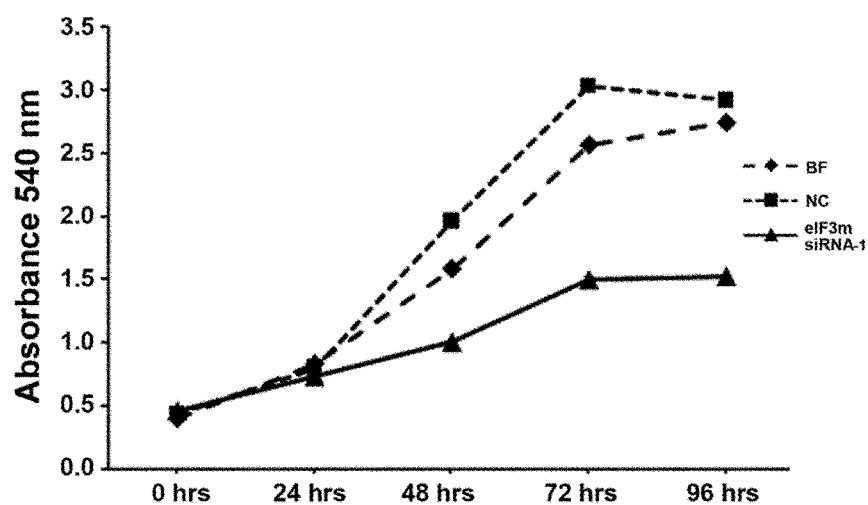

Fig. 8
a
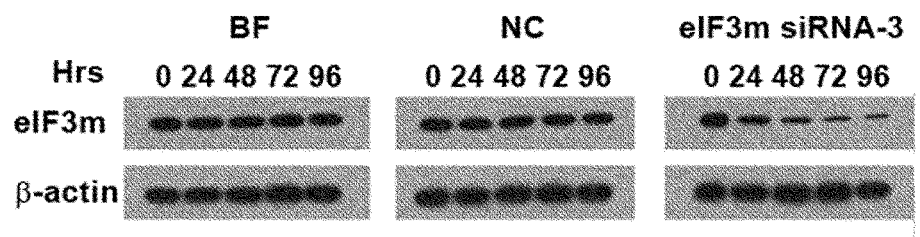
b
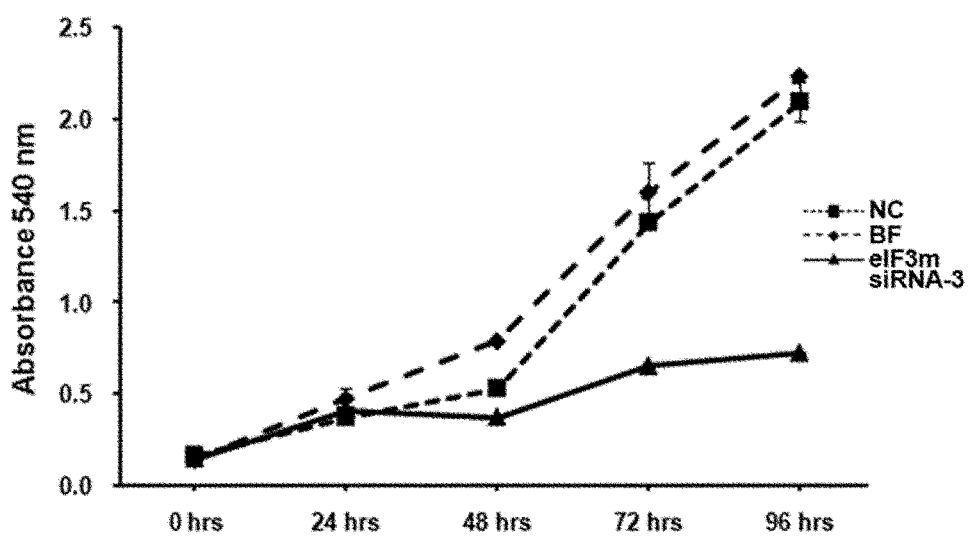

SEQUENCE LISTING

<160> NUMBER OF SEQ ID NOS: 34

<210> SEQ ID NO 1
<211> LENGTH: 20
<212> TYPE: DNA
<213> ORGANISM: Artificial
<220> FEATURE:
<223> OTHER INFORMATION: forward primer for eIF3a

<400> SEQUENCE: 1
gatcgagagg atcgcttcag                                         20

<210> SEQ ID NO 2
<211> LENGTH: 20
<212> TYPE: DNA
<213> ORGANISM: Artificial
<220> FEATURE:
<223> OTHER INFORMATION: reverse primer for eIF3a

<400> SEQUENCE: 2
catcagcacg tctccaagaa                                         20

<210> SEQ ID NO 3
<211> LENGTH: 20
<212> TYPE: DNA
<213> ORGANISM: Artificial

```
<220> FEATURE:
<223> OTHER INFORMATION: forward primer for eIF3b

<400> SEQUENCE: 3
gcctcctgca gaagaacaac                                              20

<210> SEQ ID NO 4
<211> LENGTH: 20
<212> TYPE: DNA
<213> ORGANISM: Artificial
<220> FEATURE:
<223> OTHER INFORMATION: reverse primer for eIF3b

<400> SEQUENCE: 4
cttccggaaa tcttccatca                                              20

<210> SEQ ID NO 5
<211> LENGTH: 20
<212> TYPE: DNA
<213> ORGANISM: Artificial
<220> FEATURE:
<223> OTHER INFORMATION: forward primer for eIF3c

<400> SEQUENCE: 5
gtgcctggaa gagtttgagc                                              20

<210> SEQ ID NO 6
<211> LENGTH: 20
<212> TYPE: DNA
<213> ORGANISM: Artificial
<220> FEATURE:
<223> OTHER INFORMATION: reverse primer for eIF3c

<400> SEQUENCE: 6
atcttctgac gcaaggtgct                                              20

<210> SEQ ID NO 7
<211> LENGTH: 20
<212> TYPE: DNA
<213> ORGANISM: Artificial
<220> FEATURE:
<223> OTHER INFORMATION: forward primer for eIF3d

<400> SEQUENCE: 7
cacggagctg aagaacaaca                                              20

<210> SEQ ID NO 8
<211> LENGTH: 20
<212> TYPE: DNA
<213> ORGANISM: Artificial
<220> FEATURE:
<223> OTHER INFORMATION: reverse primer for eIF3d

<400> SEQUENCE: 8
gtcaatgacg cagcgtaaaa                                              20

<210> SEQ ID NO 9
<211> LENGTH: 20
<212> TYPE: DNA
<213> ORGANISM: Artificial
<220> FEATURE:
<223> OTHER INFORMATION: forward primer for eIF3e

<400> SEQUENCE: 9
caaccaggga tggtaggatg                                              20
```

```
<210> SEQ ID NO 10
<211> LENGTH: 20
<212> TYPE: DNA
<213> ORGANISM: Artificial
<220> FEATURE:
<223> OTHER INFORMATION: reverse primer for eIF3e

<400> SEQUENCE: 10
tgcatcccaa ttctgcatta                                               20

<210> SEQ ID NO 11
<211> LENGTH: 20
<212> TYPE: DNA
<213> ORGANISM: Artificial
<220> FEATURE:
<223> OTHER INFORMATION: forward primer for eIF3f

<400> SEQUENCE: 11
ccgcacaatg agtcagaaga                                               20

<210> SEQ ID NO 12
<211> LENGTH: 20
<212> TYPE: DNA
<213> ORGANISM: Artificial
<220> FEATURE:
<223> OTHER INFORMATION: reverse primer for eIF3f

<400> SEQUENCE: 12
tgctgacgta ggctttgatg                                               20

<210> SEQ ID NO 13
<211> LENGTH: 20
<212> TYPE: DNA
<213> ORGANISM: Artificial
<220> FEATURE:
<223> OTHER INFORMATION: forward primer for eIF3g

<400> SEQUENCE: 13
ctttgccttc atcagcttcc                                               20

<210> SEQ ID NO 14
<211> LENGTH: 20
<212> TYPE: DNA
<213> ORGANISM: Artificial
<220> FEATURE:
<223> OTHER INFORMATION: reverse primer for eIF3g

<400> SEQUENCE: 14
gagctgcttt attgcccttg                                               20

<210> SEQ ID NO 15
<211> LENGTH: 20
<212> TYPE: DNA
<213> ORGANISM: Artificial
<220> FEATURE:
<223> OTHER INFORMATION: forward primer for eIF3h

<400> SEQUENCE: 15
cctcagcaca cagaggatga                                               20

<210> SEQ ID NO 16
<211> LENGTH: 20
<212> TYPE: DNA
<213> ORGANISM: Artificial
<220> FEATURE:
<223> OTHER INFORMATION: reverse primer for eIF3h

<400> SEQUENCE: 16
```
tccttgggca gttttatgg 20

<210> SEQ ID NO 17
<211> LENGTH: 20
<212> TYPE: DNA
<213> ORGANISM: Artificial
<220> FEATURE:
<223> OTHER INFORMATION: forward primer for eIF3i

<400> SEQUENCE: 17
ctctccccca actatgacca 20

<210> SEQ ID NO 18
<211> LENGTH: 20
<212> TYPE: DNA
<213> ORGANISM: Artificial
<220> FEATURE:
<223> OTHER INFORMATION: reverse primer for eIF3i

<400> SEQUENCE: 18
atcaggatgg aaggcaacac 20

<210> SEQ ID NO 19
<211> LENGTH: 20
<212> TYPE: DNA
<213> ORGANISM: Artificial
<220> FEATURE:
<223> OTHER INFORMATION: forward primer for eIF3j

<400> SEQUENCE: 19
aagcaaagca aagccaaaaa 20

<210> SEQ ID NO 20
<211> LENGTH: 20
<212> TYPE: DNA
<213> ORGANISM: Artificial
<220> FEATURE:
<223> OTHER INFORMATION: reverse primer for eIF3j

<400> SEQUENCE: 20
agggattgtg ggcaacataa 20

<210> SEQ ID NO 21
<211> LENGTH: 20
<212> TYPE: DNA
<213> ORGANISM: Artificial
<220> FEATURE:
<223> OTHER INFORMATION: forward primer for eIF3j

<400> SEQUENCE: 21
tggaatctct cgagtgcaaa 20

<210> SEQ ID NO 22
<211> LENGTH: 20
<212> TYPE: DNA
<213> ORGANISM: Artificial
<220> FEATURE:
<223> OTHER INFORMATION: reverse primer for eIF3j

<400> SEQUENCE: 22
gtgcagtttg ctgagcatgt 20

<210> SEQ ID NO 23
<211> LENGTH: 20
<212> TYPE: DNA
<213> ORGANISM: Artificial

```
<220> FEATURE:
<223> OTHER INFORMATION: forward primer for eIF3k

<400> SEQUENCE: 23
gccaaggaaa atgcctatga                                                20

<210> SEQ ID NO 24
<211> LENGTH: 20
<212> TYPE: DNA
<213> ORGANISM: Artificial
<220> FEATURE:
<223> OTHER INFORMATION: reverse primer for eIF3k

<400> SEQUENCE: 24
attggccgtt cttcttgatg                                                20

<210> SEQ ID NO 25
<211> LENGTH: 20
<212> TYPE: DNA
<213> ORGANISM: Artificial
<220> FEATURE:
<223> OTHER INFORMATION: forward primer for eIF3l

<400> SEQUENCE: 25
cttcctggac ctcacagagc                                                20

<210> SEQ ID NO 26
<211> LENGTH: 20
<212> TYPE: DNA
<213> ORGANISM: Artificial
<220> FEATURE:
<223> OTHER INFORMATION: reverse primer for eIF3l

<400> SEQUENCE: 26
tttgtggatc tgacggatga                                                20

<210> SEQ ID NO 27
<211> LENGTH: 20
<212> TYPE: DNA
<213> ORGANISM: Artificial
<220> FEATURE:
<223> OTHER INFORMATION: forward primer for eIF3m

<400> SEQUENCE: 27
tgctgcttca aaagtcatgg                                                20

<210> SEQ ID NO 28
<211> LENGTH: 20
<212> TYPE: DNA
<213> ORGANISM: Artificial
<220> FEATURE:
<223> OTHER INFORMATION: reverse primer for eIF3m

<400> SEQUENCE: 28
catgaataag ctcgccttcc                                                20

<210> SEQ ID NO 29
<211> LENGTH: 20
<212> TYPE: DNA
<213> ORGANISM: Artificial
<220> FEATURE:
<223> OTHER INFORMATION: forward primer for MIF

<400> SEQUENCE: 29
gcatcagccc ggacagggtc                                                20
```

```
<210> SEQ ID NO 30
<211> LENGTH: 20
<212> TYPE: DNA
<213> ORGANISM: Artificial
<220> FEATURE:
<223> OTHER INFORMATION: reverse primer for MIF

<400> SEQUENCE: 30
ggtggagcca gcgcagacag                                                  20

<210> SEQ ID NO 31
<211> LENGTH: 20
<212> TYPE: DNA
<213> ORGANISM: Artificial
<220> FEATURE:
<223> OTHER INFORMATION: forward primer for MT2A

<400> SEQUENCE: 31
aacccgcgtg caacctgtcc                                                  20

<210> SEQ ID NO 32
<211> LENGTH: 20
<212> TYPE: DNA
<213> ORGANISM: Artificial
<220> FEATURE:
<223> OTHER INFORMATION: reverse primer for MT2A

<400> SEQUENCE: 32
ggcacacttg gcacagccca                                                  20

<210> SEQ ID NO 33
<211> LENGTH: 18
<212> TYPE: DNA
<213> ORGANISM: Artificial
<220> FEATURE:
<223> OTHER INFORMATION: forward sequence for amplification of eIF3m

<400> SEQUENCE: 33
caccatgagg gtcccggc                                                    18

<210> SEQ ID NO 34
<211> LENGTH: 25
<212> TYPE: DNA
<213> ORGANISM: Artificial
<220> FEATURE:
<223> OTHER INFORMATION: reverse sequence for amplification of eIF3m

<400> SEQUENCE: 34
ggtatcagaa agactcaaaa ggctg                                            25
```

USE OF EIF3M FOR THE DIAGNOSIS AND TREATMENT OF CANCER

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690156_404USPC_SEQUENCE—LISTING.txt. The text file is 7 KB, was created on Sep. 28, 2011, and is being submitted electronically via EFS-Web.

TECHNICAL FIELD

The present invention relates to a cancer diagnosis composition comprising an agent for measuring an expression level of eIF3m and a composition for the treatment and prevention of cancer by regulating the expression level. More particularly, the present invention pertains to a cancer marker-detecting composition comprising an agent for measuring an mRNA or protein expression level of eIF3m, a cancer diagnosis kit comprising the same, a method for detecting an eIF3m polynucleotide or protein by treating a biological specimen with the agent to detect a substance binding specifically to the agent and quantitatively comparing the substance between a subject and a normal control, and a method for the treatment and prevention of cancer comprising an agent for down-regulating the expression of an eIF3m polynucleotide or protein.

BACKGROUND ART

Cancer is one of the most common causes of morbidity and mortality throughout the world today. Cancer incidence is expected to increase due to increasing average life expectancy, with the onset age being lowered. The ACS (American Cancer Society)'s annual Cancer Statistics article reports that in 2007, 12 million or more new cancer cases were diagnosed worldwide, with the death toll of about 7.6 million cancer patients at a death rate of about twenty thousands per day.

Lung cancer, breast cancer and colon cancer are representative of the most deadly cancer. Particularly with regard to colon cancer, its incidence of colon cancer has been dramatically increasing in South Korea. It is the fourth leading cause of cancer-related death among men in Korea, after stomach cancer, lung cancer and liver cancer. Similar rates of cancer mortality are found for women. Most cases occur among patients in their 50s, and secondly, in the 60s. The age of the greatest incidence of colon cancer in Korea is 10 years lower than that in the Western world in countries such as the U.S.A. and the Europe. In the 30s, the high incidence frequency of colon cancer accounts for 5% - 10% of all cases. Cases in the young are uncommon unless a family history of early colon cancer is present. Factors which have an influence on carcinogenesis are, for the most part, environmental, such as the westernization of the diet, particularly excess intake of animal fats and proteins, rather than heredity. Only 5% of colon cancer cases are attributed to hereditary predisposition. According to this fact and recent reports, persons with a high risk of developing colon cancer are those who 1) have been affected by colon polyps, 2) have a family history of colon cancer, 3) suffer from ulcerative colitis for a long period of time, or 4) are attacked by intractable anal fistula.

When detected at an early stage, colon cancer can be almost completely cured by endoscopic resection or surgical operation. Further, although metastasized to the liver or the lung (distant metastasis), colon cancer may still be completely cured through surgical therapy unless found too late to be operated upon. It is, however, very difficult to detect colon cancer in asymptomatic patients since the patients with colon cancer have no subjective symptoms in the early stage. In spite of inconvenience and pain, accordingly, a periodic examination must be made to detect colon cancer at the early stage which allows the surgical operation to be applied for a cure. An occult blood test is considered to be relatively convenient colon cancer screening. However, a positive response in this test is often determined to be false positive. Likewise, all negative responses do not guarantee the absence of colon cancer. That is, it is unreasonable to use the occult blood test as an accurate diagnostic method.

Leading to the present invention, intensive and thorough research into the diagnosis of and therapeutics for colon cancer, resulted in the finding that certain genes and their expression products can be used as diagnostic markers for accurately detecting colon cancer in an early stage and as targets for the treatment of colon cancer.

DISCLOSURE OF INVENTION

Technical Problem

Accordingly, it is an object of the present invention to provide a composition for detecting a cancer marker, comprising an agent for measuring an mRNA or protein expression level of eIF3m.

It is another object of the present invention to provide a cancer diagnosis kit, comprising an agent for measuring an mRNA or protein expression level of eIF3m.

It is a further object of the present invention to provide a method for detecting an eIF3m polynucleotide or protein, comprising treating a biological specimen with the agent for measuring an mRNA or protein expression level of eIF3m, detecting a complex of the agent with a polynucleotide or protein complementary thereto, and quantitatively comparing the complex between a subject and a normal control.

It is still a further object of the present invention to provide a composition for the treatment and prevention of cancer, comprising an oligonucleotide inhibitory of the expression of an eIF3m polynucleotide.

It is still another object of the present invention to provide a composition for the treatment and prevention of cancer, comprising an antibody having inhibitory activity against eIF3m polypeptide or the antigen-binding fragment thereof.

It is still yet another object of the present invention to provide a method for screening a curative drug for cancer, comprising treating a cell expressing an eIF3m polypeptide and/or polynucleotide with a candidate compound and measuring an eIF3m polypeptide or polynucleotide expression level in the cell.

Solution to Problem

In accordance with an aspect thereof, the present invention pertains to a composition for detecting a cancer marker, comprising an agent for measuring an mRNA or protein expression level of eIF3m.

The term "eIF3m", as used herein, stands for eukaryotic translation factor 3 m-subunit. eIF3 is a mammalian initiation factor with a molecular weight of as large as ~800 kDa. E1F3 is composed of 13 non-identical subunits designated eIF3a, b, c, . . . , m. Some of the subunits are known to show aberrant expression in certain cancers, but nowhere has information on the specific expression of the subunit of the present invention in certain cancers been reported in previous documents, thus far. eIF3m, also called PCID1 (PCI domain containing protein 1), was known to act as a receptor or coreceptor for entry of herpes simplex virus (HSV), but there have been no reports on the implication of the subunit in tumorigenesis and further in therapy for cancer. Moreover, in the present invention, eIF3m is first disclosed to be overexpressed in specific cancerous cell lines and cancers. The present inventors confirmed that eIF3m expression at both transcription and translation levels drastically increases in human tumor tissues as well as in human cancer cell lines. In the present invention, it is also found that eIF3m is expressed at high levels in lung cancer, breast cancer, liver cancer, leukemia, lymphoma, colon cancer, melanoma, and rectal cancer and that elevated expression levels of eIF3m are maintained in tumor regions of human colon tissues.

As used herein, the terms "marker" or "diagnosis marker" is intended to indicate a substance capable of diagnosing cancer by distinguishing cancer cells or subject suffering from cancer from normal cells or subjects, and includes organic biological molecules, quantities of which are increased or decreased in cancer cells relative to normal cells, such as polypeptides, proteins or nucleic acids (e. g., mRNA, etc.), lipids, glycolipids, glycoproteins and sugars (monosaccharides, disaccharides, oligosaccharides, etc.). With respect to the objects of the present invention, the diagnosis marker of cancer is an eIF3m polypeptide or a polynucleotide coding therefore, which are specifically expressed at high levels in cancer cells, relative to normal cells or tissues.

The term "measurement of mRNA expression levels" or corresponding phrases, as used herein, are intended to refer to a process of assessing the presence and expression levels of mRNA of cancer marker genes in biological samples to diagnose cancer, in which the amount of mRNA is measured. Analysis methods for measuring mRNA levels include, but are not limited to, RT-PCR, competitive RT-PCR, real-time RT-PCR, RNase protection assay (RPA), Northern blotting and DNA chip assay.

The term "measurement of protein expression levels" or corresponding phrases, as used herein, are intended to refer to a process of assessing the presence and expression levels of proteins expressed from colon cancer marker genes in biological samples to diagnose cancer, in which the amount of protein products of the marker genes is measured using antibodies specifically binding to the proteins. Analysis methods for measuring protein levels include, but are not limited to, Western blotting, enzyme linked immunosorbent assay (ELISA), radioimmunoassay (RIA), radioimmunodiffusion, Ouchterlony immunodiffusion, rocket immunoelectrophoresis, immunohistostaining, immunoprecipitation assay, complement fixation assay, FACS(fluorescence activated cell sorter), and protein chip assay.

The agent for measuring mRNA levels may be exemplified by a pair of primers, probes, or antisense nucleotides, which are relevant to the eIF3m polynucleotide or its fragments according to the present invention. The primers, probes, or antisense nucleotide sequences may be easily designed by those skilled in the art depending on the polynucleotide sequence of the present invention.

As used herein, the term "primer" refers to a short nucleic acid strand having a free 3' hydroxyl group, which forms a base pair with a complementary template so as to serve as a starting point for the production of a new template strand. DNA synthesis or replication requires a suitable buffer, proper temperatures, polymerizing enzyme (DNA polymerase, or reverse transcriptase), and four kinds of nucleotide triphosphates, in addition to primers. In the present invention, sense and antisense primers specific for the eIF3m polynucleotide can be used for PCR amplification so as to diagnose cancer with the PCR products. The sense and antisense primers may be altered in length suitably depending on the information known in the art.

The term "probe", as used herein, is intended to refer to a fragment of a nucleotide sequence, such as RNA or DNA, ranging in length from as short as ones bases to as long as hundreds bases, which can bind specifically to a mRNA of interest and which is tagged with a label for detecting the mRNA of interest. The probe useful in the present invention may be constructed in the form of oligonucleotide probes, single-stranded DNA probes, double-stranded DNA probes, or RNA probes. In an embodiment of the present invention, the diagnosis of cancer occurrence may be achieved by determining whether a probe complementary to the eIF3m polynucleotide of the present invention hybridizes with a nucleotide sequence of interest. Selection of suitable probes and hybridization conditions may be modified according to information known in the art.

The primers or probes useful in the present invention may be chemically synthesized using a phosphoamidite solid support method or other well-known techniques. Their nucleotide sequences may be modified using various means known in the art. Illustrative, non-limiting examples of the modification include methylation, capping, substitution of natural nucleotides with one or more homologues, and alternation between nucleotides, such as uncharged linkers (e.g., methyl phosphonate, phosphotriester, phosphoroamidate, carbamate, etc.) or charged linkers (e.g., phosphorothioate, phosphorodithioate, etc.).

Preferably, the primer or probe preferably contains 8 or more nucleotides. Hybridization may be achieved by exposing or contacting the primer or probe to the eIF3m polynucleotide of the present invention. Preferably, these sequences are hybridized with each other under such a stringent condition as to minimize non-specific pairings. In order to detect sequences which share 80% to 90% homology with the eIF3m polynucleotide of the present invention, for example, a hybridization condition may include hybridizing overnight at 42° C. in a buffer containing 0.25 M $Na_2HPO_4$, pH 7.2, 6.5% SDS, and 10% dextran sulfate and finally washing at 50° C. with a solution containing 0.1×SSC and 0.1% SDS. A stringent condition suitable for detecting a sequence which shares 90% homology with the eIF3m polynucleotide of the present invention comprises hybridizing overnight at 65° C. in 0.25M $Na_2HPO_4$, pH7.2, 6.5% SDS, 10% dextran sulfate, and finally washing at 60° C. with a solution containing 0.1×SSC and 0.1% SDS.

In accordance with an embodiment of the present invention, the agent for measuring the expression level of eIF3m protein (hereinafter, used interchangeably with "eIF3m polypeptide") is preferably an antibody.

The term "antibody", as used herein, refers to a specific protein molecule that indicates an antigenic region. With respect to the objects of the present invention, the antibody binds specifically to the marker of the present invention, that is, an eIF3m polypeptide. This antibody can be produced from a protein which the marker gene cloned typically into an expression vector encodes, using a conventional method. Also, partial peptides producible from the protein encoded by the marker gene fall within the scope of the antibody. For functioning as an antibody, the partial peptide is required to contain at least 7 amino acid residues, preferably 9 or more amino acid residues, and more preferably 12 or more amino acid residues. No particular limitations are imparted to the form of the antibodies of the present invention. Among them are polyclonal antibodies, monoclonal antibodies and fragments thereof which contain a paratope, and all immunoglobulin antibodies. Further, special antibodies such as humanized antibodies are also within the scope of the present invention. Consequently, as long as it may be produced using a method known in the art, any antibody against the eIF3m protein of the present invention can be used in the present invention.

In addition, the antibodies of the present invention which are used for detecting the diagnosis marker of cancer include functional fragments of antibody molecules as well as complete forms having two full-length light chains and two full-length heavy chains. The functional fragments of antibody molecules refer to fragments retaining at least an antigen-binding function, and include Fab, F(ab'), F(ab')2, Fv and the like.

As used herein, the term "cancer" refers to a class of diseases in connection with the regulation of cell death, in which a group of cells display uncontrolled overgrowth, resulting from insufficient apopotosis. The excessively growing cells invade adjacent tissues and organs to destroy and deform normal structures, forming tumoral mass, the state of which is defined as cancer. As a rule, tumor is a neoplasm or a solid lesion formed by an abnormal excessive growth of cells. A tumor may be benign or malignant. Malignant tumors, which typically grow far faster than do benign tumors, invade adjacent tissues and sometimes metastasize, threatening the life. The malignant tumor is typically regarded as cancer. Examples of the cancers detectable with the composition for detecting a cancer marker in accordance with the present invention include cephaloma, head and neck cancer, lung cancer, breast cancer, thymoma, mesothelioma, esophageal cancer, pancreatic cancer, colon cancer, liver cancer, stomach cancer, cholangiocarcinoma, kidney cancer, bladder, prostate cancer, testicular cancer, spermocytoma, ovarian cancer, uterine cervical cancer, endometrial cancer, lymphoma, acute leukemia, chromic leukemia, multiple myeloma, sarcoma, and malignant melanoma, but are not limited thereto. In a preferred embodiment of the present invention, the composition for detecting a cancer marker is applied to lung cancer, liver cancer, colon cancer, breast cancer, leukemia, lymphoma and melanoma cell lines to examine the expression level of the cancer marker therein. When the composition was applied, the eIF3m protein was observed to have remarkably higher expression levels in tissues from subjects with cancer than in those from normal subjects.

In accordance with another aspect thereof, the present invention provides a cancer diagnosis kit that comprises an agent for measuring an mRNA or protein expression level of eIF3m.

The term "diagnosis" in the context of the present invention, refers to a process of determining the presence or absence of the eIF3m polypeptide or polynucleotide of the present invention in a biological specimen or a tissue sample so as to identify the existence or characteristics of a disease related to the expression of the gene.

The detection of cancer marker may be accomplished by determining the expression level of the eIF3m polypeptide or a polynucleotide encoding it using the kit of the present invention. The kit of the present invention may comprise a primer or probe for measuring the expression level of the cancer diagnosis marker, an antibody selectively recognizing the cancer marker or its fragments retaining an antigen-binding function, and/or one or more agents or compositions suitable for the analysis of the polypeptide or polynucleotide. For example, the diagnosis kit for the quantitative analysis of the polynucleotide or gene of the present invention may comprise at least one oligonucleotide specifically binding to a polynucleotide coding for the eIF3m polypeptide. In a preferable embodiment, the diagnosis kit of the present invention is characterized by including essential elements required for performing RT-PCR. An RT-PCR kit includes a pair of primers specific for the nucleotide sequence of eIF3m or its partial sequence, reverse transcriptase, Taq polymerase, PCR primers, and dNTP. As long as it takes advantage of analysis methods known in the context of 'measurement of mRNA expression level' any kit may be employed without limitations.

In another preferable embodiment, the cancer diagnosis kit of the present invention may comprise an antibody specifically binding to the eIF3m protein of the present invention. As long as it takes advantage of analysis methods known in the context of 'measurement of protein expression level', any kit may be employed without limitations. Preferable is an ELISA kit or a protein chip kit.

The measurement of protein expression level using an antibody is based on the formation of an antigen-antibody complex between the eIF3m protein and an antibody thereto. Leading to determining the protein expression level, the amount of the antigen-antibody can be measured using various methods.

As used herein, the term "antigen-antibody complex" is intended to refer to binding products of a cancer marker protein to an antibody specific thereto. The antigen-antibody complex thus formed may be quantitatively determined by measuring the signal size of a detection label.

For instance, cancer can be diagnosed by determining a significant increase in eIF3m protein expression level in a suspected subject from the comparison of the amount of antibody-antigen complex between the suspected subject and a normal control. In this regard, a sample from a subject with suspected cancer is treated with an antibody specific for the eIF3m protein of the present invention to form an antigen-antibody complex which can be quantitatively analyzed using a kit on the basis of an ELISA assay, an RIA assay, a sandwich ELISA assay, a Western blotting assay, a radioimmunodiffusion assay, an ouchterlony immunodiffusion assay, a rocket immunoelectrophoresis assay, an immunohistostaining assay, an immunoprecipitation assay, a complement fixation assay, FACS, a protein chip assay or an immunodot assay. Comparison of the analysis data with those of normal subject allows the diagnosis of cancer in connection with an increase in eIF3m protein expression.

In accordance with a further aspect thereof, the present invention pertains to a method for detecting an eIF3m polynucleotide or protein, comprising treating a biological specimen with the agent for measuring an mRNA or protein expression level of eIF3m, detecting a complex of the agent with a polynucleotide or protein complementary thereto, and quantitatively comparing the complex between a subject and a normal control.

In detail, the expression of a gene may be detected at an mRNA or a protein level. mRNA or protein isolation from a biological specimen may be achieved using a well-known method.

As used therein, the term "biological specimen" is intended to refer to a sample from which a gene or protein expression level of eIF3m can be measured. Examples of the biological specimen useful in the present invention include tissues, cells, whole blood, serum, plasma, saliva, sputum, cerebrospinal fluid and urine, but are not limited thereto.

In an embodiment of the detecting method according to the present invention, a gene expression level in a subject with suspected cancer can be compared to that in a normal control to diagnose cancer incidence in the subject. In detail, a biological sample from a subject with suspected cancer is measured for the expression level of the marker of the present invention. This level is compared with that measured in a biological sample from a normal control. When the expression level of the marker of the present invention is higher in the subject than in the normal control, the subject may be determined to be affected by cancer.

In the case where a polynuceotide coding for the eIF3m polypeptide of the present invention is used as a marker, the method comprises (a) providing a biological specimen; (b) treating the biological specimen with an agent for measuring an expression level of eIF3m; (c) detecting a binding product of the agent to a polynucleotide complementary to the agent; and (d) quantitatively comparing the binding product between a subject and a normal control. In the case where the eIF3m polypeptide of the present invention is used as a marker, the method comprises (a) providing a biological specimen; (b) treating the biological specimen with an antibody specific for the eIF3m protein; (c) detecting an antigen-antibody complex; and (d) quantitatively comparing the complex between a subject and a normal control.

In accordance with still a further aspect thereof, the present invention pertains to a composition for the treatment and prevention of cancer, comprising as an active ingredient an oligonucleotide inhibitory of the expression of an eIF3m polynucleotide or an antibody inhibiting the activity of eIF3m polypeptide or an antigen-binding fragment thereof.

In a preferred embodiment of this aspect the pharmaceutical composition may include a substance inhibiting the expression of eIF3m polynucleotide of the present invention. The eIF3m expression inhibitor substance may be selected from the group consisting of siRNA, shRNA, an aptamer and an antisense oligonucleotide.

As used herein, the term "siRNA (small interfering RNA)" is intended to refer to a small nucleic acid molecule of about 20 nucleotides, which mediates RNA interference or gene silencing. When siRNA is introduced into a cell, it is recognized by dicer to degrade the gene encoding the eIF3m, resulting in the specific knockdown of an eIF3m gene.

The term "shRNA" refers to a short hairpin RNA in which sense and antisense sequences of an siRNA target sequence are separated by a loop structure of 5 to 9 bases.

As used herein, the term "aptamer" refers to an oligoribonucleic acid molecule which is 20 to 60 nt long. It has various three-dimensional structures depending on sequences and binds to a specific target molecule to effectively regulate the function of the target molecule.

Recently, the phenomenon of RNA interference (RNAi) has been studied for application to a method for controlling protein expression at the gene level. Typically, siRNA has been shown to inhibit protein expression by binding specifically to mRNA, having a sequence complementary to a target gene.

In order to interfere with the expression of oncogenes or metastagenes, the composition comprising siRNA or shRNA according to the present invention may be administered to a subject according to a typical method adopted for use in the gene therapy based on these RNAs. For instance, gene expression can be regulated by low-volume intravenous injection of siRNAs according to the method described by Filleur et al., Cancer Res., 63(14): 3919-22, 2003. In order to increase the cellular uptake and stability of siRNAs, siRNA may also be injected in conjunction with a conjugate according to Chien et al., Cancer Gene Ther., 12(3) 321-8, 2005.

The short interfering RNA molecules (siRNA) contained in the present composition can be prepared by direct chemical synthesis (Sui G et. al, (2002) *Proc Natl Acad Sci* USA 99:5515-5520) or in vitro transcription (BrummelkampTR et al., (2002) *Science* 296:550-553), but the present invention is not limited to these methods. Also, shRNAs, which are designed to overcome the drawbacks of siRNAs, including expensive siRNA biosynthesis and low transfection efficiency, leading to the short-term persistence of the RNA interference effect, can be expressed from a RNA polymerase III-based promoter contained in an adenoviral, rentiviral or plasmid expression vector system, that has been introduced into cells. The shRNA molecules are processed to functional siRNA molecules using an siRNA processing enzyme (Dicer or RNase III) within the cells, and then the silencing of a target gene is induced.

As used herein, the term "antisense" is intended to refer to an oligomer having a sequence of nucleotide bases and a subunit-to-subunit backbone that allows the antisense oligomer to hybridize with a target sequence in RNA by Watson-Crick base pairing to form an RNA:oligomer heteroduplex within the target sequence, typically with mRNA. The oligomer may have exact sequence complementarity to the target sequence, or near complementarity thereto. These antisense oligomers may block or inhibit the translation of the mRNA, and/or modify the processing of mRNA to produce a splice variant of the mRNA. Thus, the antisense oligomer of the present invention is an antisense oligomer complementary to a polynucleotide coding for the eIF3m polypeptide. For gene therapy, the antisense oligonucleotide according to the presence invention may be administered by a typical method. The administration of the composition may lead to preventing or suppressing oncogene expression. For instance, an antisense oligodeoxynucleotide is loaded onto a microparticle carrier based on poly-L-lysine by electrostatic attraction as described in J. S. kim et al., J controlled Release 53, 175-182 (1998) and the oligonucleotide-loaded microparticle is injected intravenously, but the present invention is not limited to this method.

Preferably, the composition according to the present invention may include a known therapeutic agent, which is directly or indirectly conjugated to the agent or is present in an unconjugated form. The therapeutic agent capable of binding to the antibody includes, but is not limited to, radionuclides, drugs, lymphokines, toxins and bispecific antibodies. As long as it can exert therapeutic effects on cancer when conjugated to an antibody or administered in combination with an siRNA, an shRNA or an antisense oligonucleotide, any known therapeutic agent can be used in the present invention.

Examples of the radionuclides include, but are not limited to, $^{3}H, ^{14}C, ^{32}P, ^{35}S, ^{36}Cl, ^{51}Cr, ^{57}Co, ^{58}Co, ^{59}Fe, ^{90}Y, ^{125}I, ^{131}I$, and $^{186}Re$.

The drugs and toxins useful in the present invention include etoposide, teniposide, adriamycin, daunomycin, carminomycin, aminopterin, dactinomycin, mitomycin, cis-platinum and cis-platinum analogues, bleomycins, esperamicins, 5-fluorouracil, melphalan, and nitrogen mustard, but are not limited thereto.

eIF3m-specific siRNAs are examined for activity of inhibiting oncogenesis by suppressing eIF3m gene or protein expression. Comparison with a control indicated that expression patterns relevant to cell growth and cell cycle were regulated.

In a preferred embodiment thereof, the present invention provides a composition comprising a substance inhibiting the activity of the eIF3m protein. Preferably, the activity-inhibiting substance is an antibody that specifically recognizes an eIF3m protein. The antibody includes all monoclonal antibodies and chimeric antibodies, humanized antibodies and human antibodies thereof. As long as they have the binding property of specifically recognizing eIF3m, the antibodies include complete forms having two full-length light chains and two full-length heavy chains, or may be in the form of functional fragments of antibody molecules. As used herein, the term "functional fragments of antibody molecules" is intended to refer to fragments retaining at least an antigen-binding function, which are exemplified by Fab, F(ab'), F(ab)$_2$ and Fv.

Preferably, the composition according to the present invention may include an acceptable carrier appropriate to the administration mode thereof.

The active ingredient may be combined with pharmaceutically acceptable vehicles, excipients, or additives. Examples of the pharmaceutically acceptable carriers useful in the present invention include physiological saline, sterile water, Ringer s solution, buffered saline, dextrose solution, maltodextrin solution, glycerol, ethanol, and liposomes. They may be used alone or in combination. If necessary, the composition may further comprise other typical additives such as antioxidants, buffers, etc. Depending on administration mode, the composition may be formulated with a diluent, a dispersant, a surfactant, a binder and/or a lubricant into an injection dosage form such as aqueous solution, suspension, emulsion, etc. or an oral dosage form such as pill, capsule, granule, tablet, etc. When conjugated with the carrier, an antibody or ligand specific for target organs or tissues may direct the active ingredient toward the organs or tissues. Typical vehicles, excipients and additives known in the art may be used in the present invention. The present invention is not limited to the examples of vehicles, excipients and additives.

The composition or formulation may be administered in a therapeutically effective amount to subjects through a suitable route according to purpose or necessity. The pharmaceutical composition may be administered orally, parenterally, subcutaneously, intraperitoneally, or intranasally. For local immunosuppressive therapy, the composition may, if desired, be administered using a suitable method, including intralesional administration. Parenteral injections include intramuscular, intravenous, intraarterial, intraperitoneal and subcutaneous routes. The therapeutically effective amount of the composition comprising the antisense oligonucleotide, siRNA or shRNA may vary depending on various factors well known in the medical art, including the kind and degree of the response to be achieved, the patient's age, body weight, and state of health, etc.

In accordance with still yet another aspect thereof, the present invention is directed to a method for screening a curative agent for cancer, comprising treating a cell expressing an eIF3m polypeptide and/or polynucleotide with a candidate compound and measuring an eIF3m polypeptide or polynucleotide expression level in the cell.

In the screening method of the present invention, the candidate compound, if inducing an increase in eIF3m expression level, is determined as being oncogenic. When the eIF3m expression level is reduced thereby, the candidate compound is determined as a possible therapeutic agent for cancer. According to the screening method, the activity of the candidate can be easily determined by the eIF3m expression level.

Advantageous Effects of Invention

As described hitherto, eIF3m can be used as a cancer marker which allows cancer to be diagnosed with high sensitivity and specificity. Particularly, the cancer marker is useful for the diagnosis of lung cancer, breast cancer, liver cancer, leukemia, lymphoma, rectal cancer, melanoma, and colon cancer. Furthermore, when administered to a subject, an eIF3m expression regulator can prevent the onset or progress of cancer by inhibiting the overexpression of the eIF3m gene.

BRIEF DESCRIPTION OF DRAWINGS

FIG. 4 shows Northern blots of eIF3m in normal human tissues and human cancer cell lines.

FIG. 7 shows that silencing of eIF3m expression by siRNA results in the reduction of cell proliferation rate. The eIF3m siRNA-1 transfected HCT-116 (wt) cells were incubated for 96 hours. Negative controls included buffer alone-no siRNA (BF) and non-human negative control siRNA (NC).

FIG. 8 shows that silencing of eIF3m expression by siRNA-3 results in the reduction of cell proliferation. The eIF3m siRNA-3 transfected HCT-116 (wt) cells were incubated for 96 hours. Negative controls included buffer alone-no siRNA (BF) and non-human negative control siRNA (NC).

MODE FOR THE INVENTION

Figure 1:
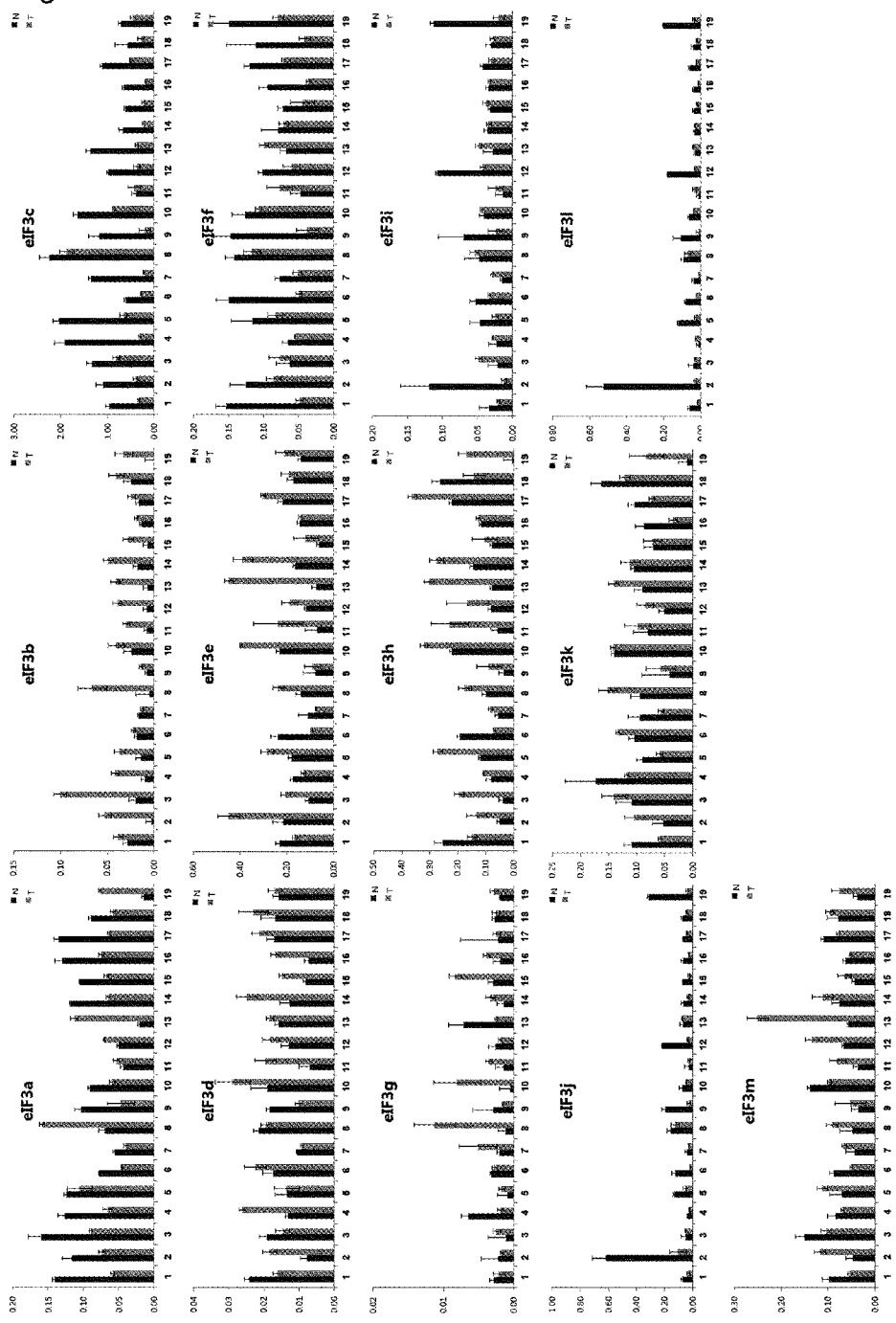
FIG. 1 shows expression levels of eIF3 subunits in paired patient tissues. All the qRT-PCR reactions were carried out using primers listed on Table 1 and quantified by AQ method.

A better understanding of the present invention may be obtained through the following examples which are set forth to illustrate, but are not to be construed as limiting the present invention.

EXAMPLE 1

Colon Tissue

Human colon tissues were obtained in compliance with the Helsinki Treaty. Tissues were excised from patients according to the protocol and stored at −80° C. until use.

EXAMPLE 2

Cell Culture

All of the cell lines used in the present invention were obtained from the ATCC (American Type Culture Collection, Manassas, Va.) and the Korean Cell Line Bank (Seoul, Korea). Each cell line was maintained in a maintenance medium supplemented with 10% FBS (fetal bovine serum, Invitrogen).

EXAMPLE 3

Real-time Quantitative RT-PCR

Total RNA was extracted washed using Trizol reagent (Invitrogen) according to the manufacturer's instruction. The isolate was treated with DNase Ito remove residual genomic DNA, followed by purification through RNeasy column (Qiagen). RNA was quantified using Nanodrop 1000 (Thermo Scientific). Micrograms of the total RNA were used for cDNA synthesis using 1 μl of 50 μM oligo(dT) as a primer in 50 mM Tris-Hcl (pH 8.3), followed by reverse transcription by Superscript III transcriptase (Invitrogen) in 20 μl of an RT mix containing 75 mM KCl, 3 mM $MgCl_2$, 5 mM DTT, 0.5 mM dNTP, and 40 U RNase Out (Invitrogen). The template RNA was removed by incubation at 37° C. for 20 min with 1 μl of RNaseH (2 units). A standard curve was generated from a 10-fold serial dilution of the amplicon cloned into pCR2.1 TOPO ranging from $1.0 \times 10^{10}$ copies/μl to $1.0 \times 10^2$ copies/μl. Real-time PCR analyses were carried out with 1/10 of the cDNA synthesized by Superscript RT III (Invitrogen, USA) and 5 pmoles of forward and reverse primers (Table 1) in a QuantiFast SYBR Green PCR master mix (Qiagen, Germany) with the following thermal profile: 50° C. 2 min hold, 95° C. 10 min hold, 95° C. 30 sec −58° C. 30 sec −72° C. 30 sec repeated for 40 cycles on LightCycler480 (Roche Applied Science, Switzerland). Data was analyzed by either relative quantification(RQ) normalized with GAPDH or ACTB, or absolute quantification (AQ) method.

TABLE 1

| NAME | SEQUENCE (5' -> 3') | SEQ ID No. |
|---|---|---|
| EIF3A-F | GATCGAGAGGATCGCTTCAG | 1 |
| EIF3A-R | CATCAGCACGTCTCCAAGAA | 2 |
| EIF3B-F | GCCTCCTGCAGAAGAACAAC | 3 |
| EIF3B-R | CTTCCGGAAATCTTCCATCA | 4 |
| EIF3C-F | GTGCCTGGAAGAGTTTGAGC | 5 |
| EIF3C-R | ATCTTCTGACGCAAGGTGCT | 6 |
| EIF3D-F | CACGGAGCTGAAGAACAACA | 7 |
| EIF3D-R | GTCAATGACGCAGCGTAAAA | 8 |
| EIF3E-F | CAACCAGGGATGGTAGGATG | 9 |
| EIF3E-R | TGCATCCCAATTCTGCATTA | 10 |
| EIF3F-F | CCGCACAATGAGTCAGAAGA | 11 |
| EIF3F-R | TGCTGACGTAGGCTTTGATG | 12 |
| EIF3G-F | CTTTGCCTTCATCAGCTTCC | 13 |
| EIF3G-R | GAGCTGCTTTATTGCCCTTG | 14 |
| EIF3H-F | CCTCAGCACACAGAGGATGA | 15 |
| EIF3H-R | TCCTTGGGCAGTTTTTATGG | 16 |
| EIF3I-F | CTCTCCCCCAACTATGACCA | 17 |
| EIF3I-R | ATCAGGATGGAAGGCAACAC | 18 |
| EIF3J-F | AAGCAAAGCAAAGCCAAAAA | 19 |
| EIF3J-R | AGGGATTGTGGGCAACATAA | 20 |
| EIF3J-F | TGGAATCTCTCGAGTGCAAA | 21 |
| EIF3J-R | GTGCAGTTTGCTGAGCATGT | 22 |
| EIF3K-F | GCCAAGGAAAATGCCTATGA | 23 |
| EIF3K-R | ATTGGCCGTTCTTCTTGATG | 24 |
| EIF3L-F | CTTCCTGGACCTCACAGAGC | 25 |
| EIF3L-R | TTTGTGGATCTGACGGATGA | 26 |
| EIF3M-F | TGCTGCTTCAAAAGTCATGG | 27 |
| EIF3M-R | CATGAATAAGCTCGCCTTCC | 28 |
| MIF-F | GCATCAGCCCGGACAGGGTC | 29 |
| MIF-R | GGTGGAGCCAGCGCAGACAG | 30 |
| MT2A-F | AACCCGCGTGCAACCTGTCC | 31 |
| MT2A-R | GGCACACTTGGCACAGCCCA | 32 |

EXAMPLE 4

Norhern Blotting

The 1,126 bp-long open reading frame of the full-length EIF3m gene was labeled with [alpha-$^{32}$P] dCTP (3000

Ci/mmol, 10 mCi/ml; Perkin Elmer NEN) by RediPrime kit (GE Healthcare, USA) and filtered through G-50 Microcolumn (GE Healthcare, USA) to remove unbound nucleotides. MTN blot (BD clontech, USA) was hybridized at 42° C. overnight with denatured probes in an ULTRAhyb solution (Ambion, USA), and detected on a BioMax MS film (Kodak, USA)according to the standard protocol with the screen intensified at −80° C.

EXAMPLE 5

Western Blotting

Cell lysates were prepared by homogenizing cultured cells in an M-PER lysis buffer containing a Halt protease inhibitor (Thermo Scientific, USA). Tissue lysates were prepared by homogenizing sliced tissues in a T-PER lysis buffer containing a Halt protease inhibitor (Thermo Scientific, USA). Tissue homogenates were prepared by mixing tungsten beads at 30 Hz for 2 min in microtubes with the aid of TissueLyser (Qiagen). Protein concentrations were measured using a BCA protein assay kit (Thermo Scientific) according to the manufacturer's instruction. The cell or tissue lysates were resolved on 4-12% NuPAGE gel (Invitrogen) in 1× MOPS running buffer by electrophoresis and then transferred onto Immobilon-P membrane (Millipore, USA), followed detection with 1:2,000 diluted primary anti-eIF3m antibody (Proteintech Group) or 1:500 diluted anti-MIF antibody (Abnova), and finally HRP-conjugated anti-rabbit antibody (Sigma-Aldrich).

EXAMPLE 6

Immunohistochemistry

Tumor tissues of the colon were fixed in a 10% neutral buffered formalin solution and embedded in paraffin blocks according to the standard procedure. 4 µm-thick tissue slices were mounted on slides and were pretreated with proteinase. Staining was conducted using a BechMark XT automated system (Ventana Medical System). A primary antibody for Western blotting was applied at 1:100 dilution and masked with endogenous biotin to avoid the detection of false positive signal. Signals were detected by biotinylated secondary antibodies, followed by binding a streptavidin-HRP (horseradish peroxidase) conjugate thereto. The complex was visualized as dark brown precipitates with a hydrogen peroxide substrate and 3,3'-DAB (diaminobenzidine tetrahydrochloride) chromogen The slides were counterstained with hematoxylin-eosin and observed under an optical microscope.

EXAMPLE 7

Cloning of Tagged eIF3m

The eIF3m ORF was amplified with primers having the following nucleotide sequences and inserted into a pCR2.1-TOPO vector.

```
                                       (SEQ ID NO. 33)
F: 5'-CAC CAT GAG GGT CCC GGC-3'

(SEQ ID NO. 34)
R: 5'-GGT ATC AGA AAG ACT CAA AAG GCT G-3'
```

After being sequenced, the insert was cloned into a pFLAG-CMV2 vector (Sigma-Aldrich).

EXAMPLE 8

Ribonomics

Two million HCT-116 cells were transfected with 4 µg of the pFLAG-CMV2-eIF3m expression vector by Lipofectamine 2000 (Invitrogen) and cultured for 48 hrs at 37° C. in DMEM supplemented with 10% FBS in a 5% $CO_2$ incubator. The cells were homogenized in Symplekin immunoprecipitation buffer (150 mM NaCl, 25 mM HEPES-KOH [pH 7.5], 10% [v/v] glycerol, 1 mM $MgCl_2$, 2 mM sodium orthovanadate, 2 mM β-glycerophosphate, 1 mM PMSF (phenylmethylsulphonylfluoride), 1 mM DTT, 2 mM EDTA, 0.5% TritonX-100, 50 µg/ml RNaseA [Sigma-Aldrich], and 1× protease inhibitor cocktail [Roche]). The lysate was washed, centrifuged, and precipitated with 40 µl of FLAG-M2 affinity gel. Total RNA was extracted from immunoprecipitated gel pellet using Trizol reagent according to the protocol provided by the manufacturer. The total RNA was quantified with Nanodrop 1000. 1.575 µg of total RNA was used for making cDNA library by GeneRacer kit (Invitrogen). The total RNA was dephosphorylated, decapped and ligated to an RNA adaptor before reverse transcription. Using GeneRacer 5' and 3' primers specific for the adaptor, PCR was performed with 24 cycles of the following thermal profiles. The PCR product was cloned into an EcoRV-digested pBlueScriptll-KS(+) vector and transformed into DH10B competent cells by electroporation. Cells from single colonies were identified and each clone was sequenced.

EXAMPLE 9

Cell Proliferation and Cell Cycle Analysis

The effects of eIF3m on cell proliferation and cell cycle were assayed after the treatment of the wild-type human colon cancer cell line HCT-116 with siRNAs which were designed in advance from Qiagen. 20,000 HCT-116 cells were transfected with eIF3m-specific siRNA, or negative control siRNA (NC) or RNase-free buffer only (BF) and cultured for 96 hours in 6-well plates, with monitoring for cell proliferation by MTT (3-[4,5-dimethylthiazol-2-yl]-2,5-diphenyltetrazolium bromide) assay every 24 hours. The three kinds of HCT-116 cell cultures with non-specific control siRNA, eIF3m-specific siRNA and RNase-free buffer only (untreated 100% survival control) were transected and plated onto 6-well plates. 725 µL of MTT (2 mg/ml) was added to each well every hour. After incubation for 4 hrs, the medium was aspirated off and the cells were incubated for 10 min with 1.955 ml of DMSO (dimethyl sulfoxide). Absorbance at 540 nm was read on a scanning microplate reader (Molecular Devices). Cell cycle progression was analyzed through flow cytometry. Approximately $5 \times 10^4$ HCT-116 cells were seeded onto 6-well plates and treated with negative control siRNA, eIF3m-specific siRNA or RNase-free buffer only. Cells were collected by treatment with 0.5% trypsin every hour, washed with ice-cold PBS and fixed at 4° C. with 70% ethanol. Then, the cells were washed and resuspended at 37° C. for 20 min in propidium iodide (PI) staining buffer (10 µg/ml DNase-free RNase A, 50 µg/ml PI in PBS). The PT-stained cells were analyzed using BD Cellquest software on FAC-SCalibur™ Flow Cytometer (BD Biosciences, USA).

eIF3m expression was found to be reduced (knockdown), as monitored by Western blotting.

EXAMPLE 10

Assessment of Statistical Significance

Figure 2:
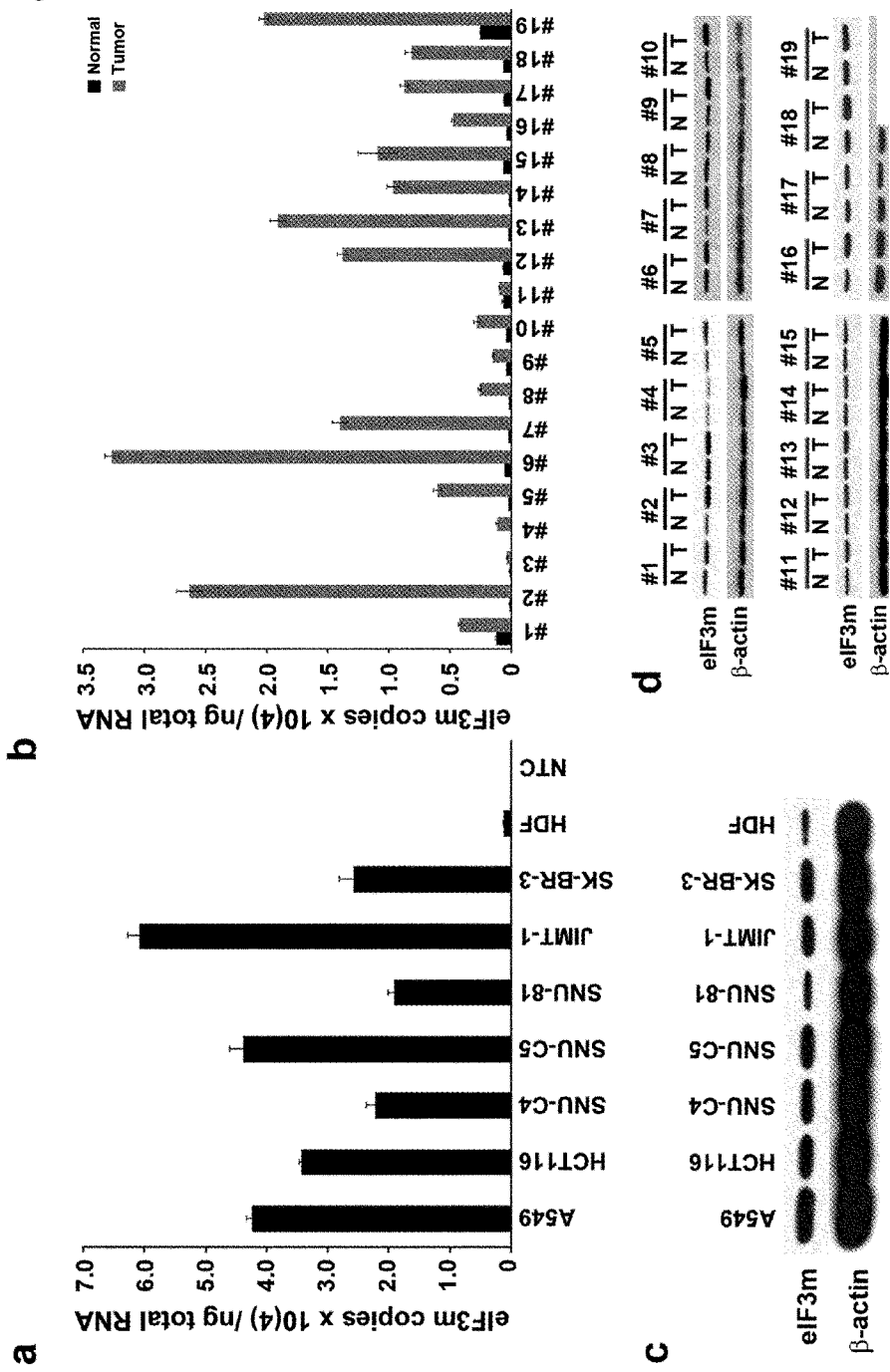
FIG. 2 shows the expression of eIF3m (eukaryotic translation factor 3 m-subunit) in cancer cell lines and human colon tissues.

The statistical significance was analyzed by Student's two-tail t-test for comparison between unpaired groups and Student's paired two-tail t-test for comparison between normal/tumor tissue pairs. For displaying error range we adopt standard deviation or standard error mean (SEM) for each group Results Elevated Expression of eIF3m Subunits in Cancer To examine relationship between the upregulation of eIF3m subunit and the progression of human colon tumor, real-time PCR was first performed to detect transcripts of 13 eIF3 subunits in pairs of normal colon and tumor (adenocarcinoma) tissues from 19 patients. Expression differences were measured by relative quantification (RQ) normalized by GAPDH (FIG. 1). eIF3b, one of the eIF3 core subunits, showed high expression levels in most of the patients (18/19) whereas the other core factors remained low in expression level. Among the eight non-core subunits, eIF3d, e, h, k and in subunits showed elevated expression in tumors of more than 50% of patients. Of the five non-core eIF3 subunits showing higher expression in tumors, eIF3m was chosen for further study on characteristics thereof. In order to confirm the elevated eIF3m expression in tumors, all the same patients as well as seven kinds of cultured cancer cell lines were measured for eIF3m mRNA levels by absolute quantification (AQ). A standard curve (correlation coefficient $r^2>0.95$) was drawn, and used to calculate the numbers of molecule (FIG. 2A). The lung cancer cell line, A549, showed $4.25\times10^4$ copies/ng total RNA. In four colon cancer cell lines, the expression ranged from $1.92\times10^4$ to $3.44\times10$ copiesing total RNA. In two breast cancer cell lines, especially in Herceptin resistant JIMT-1, the expression level ($6.09\times10^4$ copies/ng total RNA) was more than double of the Herceptin sensitive SK-BR-3($2.57\times10^4$ copies/ngtotalRNA). In contrast to those seven human cancer cell lines, the normal cell line HDF showed a very low expression level ($1.17\times10^3$ copies/ng total RNA). While the RQ data showed higher expression in tumors in 12 out of 19 patients, AQ showed markedly elevated expression of eIF3m in tumors in all patients (paired t-test p=0.00013) ranging from $3.44\times10^2$ to $3.27\times10^4$ copies/ng total RNA compared to the normal counterparts which ranged from $3.50\times10$ to $2.51\times10^3$ (FIG. 2B). Also, elevated protein levels of eIF3m were confirmed in the cell lines and tissue pairs. Cancer cell lines expressed higher protein levels of eIF3m than did normal cell line HDF, with the correspondence of their expression intensities with mRNA levels (FIG. 2C). The eIF3m expression in two breast cancer cell lines at protein level was similar to the mRNA levels described above. There is a difference in eIF3m protein expression between normal and tumorous colon tissue, which was however not as dramatic as in the mRNA levels (FIG. 2D).

Figure 3:
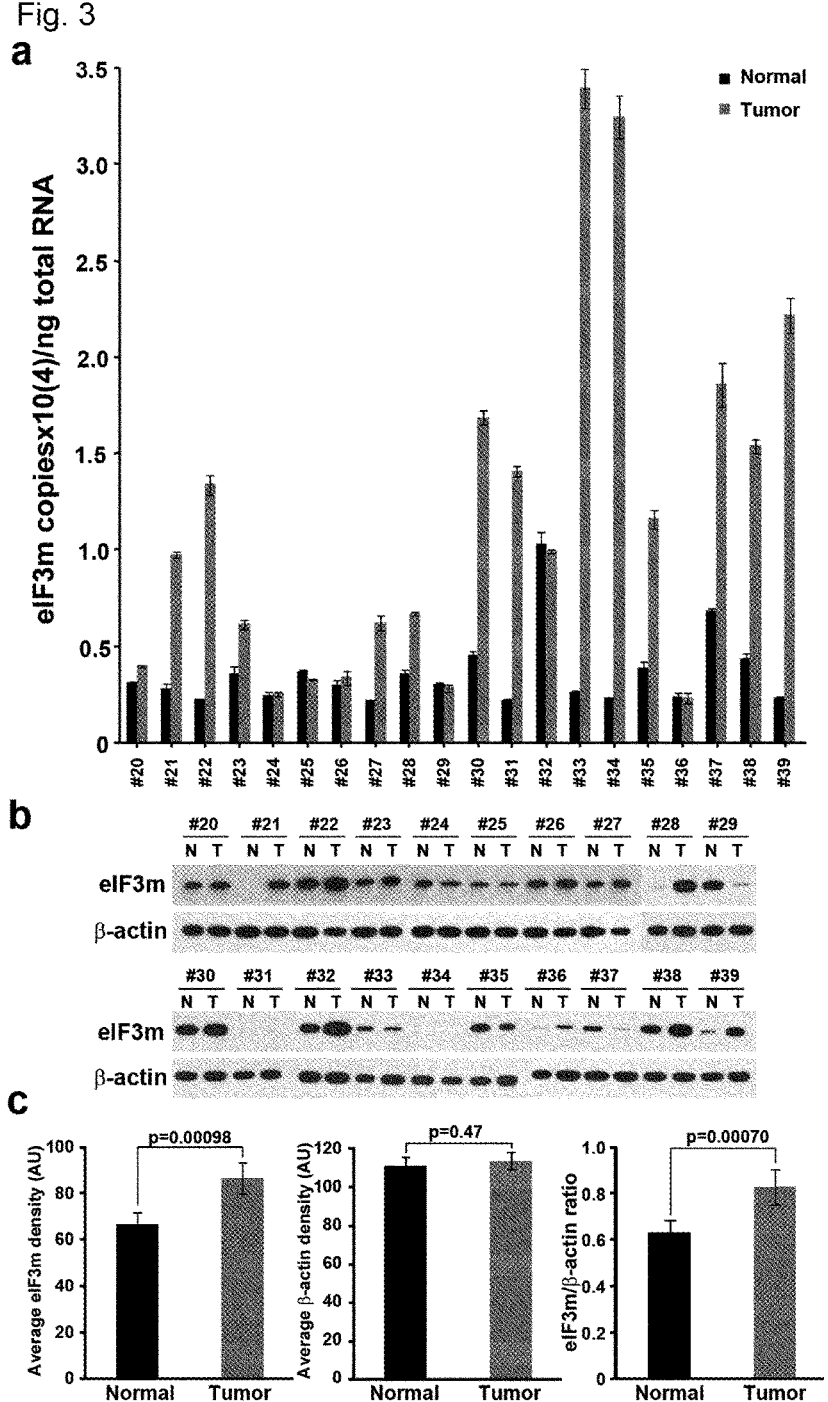
FIG. 3 shows elevated expression of eIF3m in patient samples. Twenty pairs of normal-tumor tissues from colon adenocarcinoma patients were analyzed for their eIF3m expression at transcription level by qRT-PCR.

To make sure of its expression difference, we checked its mRNA and protein levels (FIGS. 3A and 3B) in 20 additional paired patient tissues. Then protein expression difference was evaluated between normal and tumor tissues by densitometry (FIG. 3C). The average density of eIF3m itself in tumor tissues (86.6) was 1.3 fold higher than in normal counterpart (66.6) (paired t-test p=0.00098). The fold change of normalized density by beta-actin was also 1.3 (p=0.00070).

Data obtained from the analysis imply that the elevated expression level of eIF3m is associated with tumor progression in cell lines as well as in colon tissues.

Tissue Specificity of eIF3m mRNA Expression

The tumor specificity of eIF3m expression was examined at a transcription level by Northern hybridization. While the normal tissues, heart, skeletal muscle, kidney, liver, placenta, and peripheral blood leukocytes showed elevated eIF3m expression, no detectable expression signals of eIF3m were found in brain, colon, thymus, small intestine, and lung. β-actin, serving as a housekeeping gene, was consistently present in all these tissues (FIG. 4A). Human cancer cell lines also showed high expression of eIF3m mRNA (FIG. 4B). Very high expression levels of eIF3m were observed in several leukemia cell lines and lymphoma cell lines. The colorectal adenocarcinoma SW480 was higher in eIF3m expression than was melanoma. Also, the lung carcinoma cell line A549 was found to have an eIF3m expression level as measured by qRT-PCR. In this hybridization no splice variants of the eIF3m transcript was found.

Figure 5:
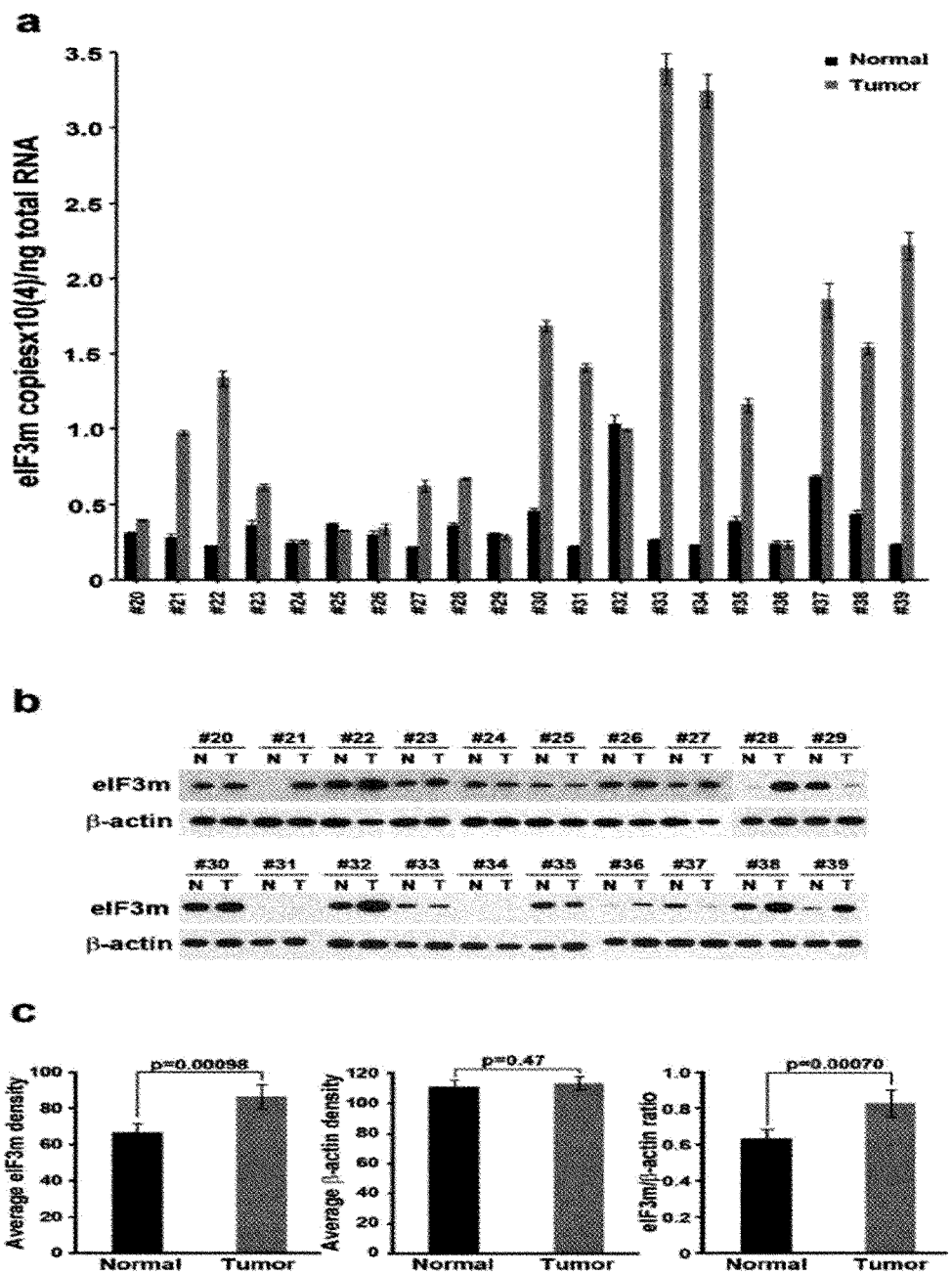
FIG. 5 shows data of qRT-PCR and Western blotting with normal/tumor tissue pairs from colon cancer patients.

Normal/tumor tissue pairs from colorectal adenocarcinoma patients were assayed for eIF3m expression at a transcription level by qRT-PCR (FIG. 5). Tumor tissues from most of the patients were observed to significantly increase in eIF3m mRNA level, with approximately 10-fold higher expression levels than in normal tissues in some patients (FIG. 5A #33 and #34). In a Western blotting analysis, significantly thick bands were detected compared to those of normal tissues. (FIG. 5B)

Figure 6:
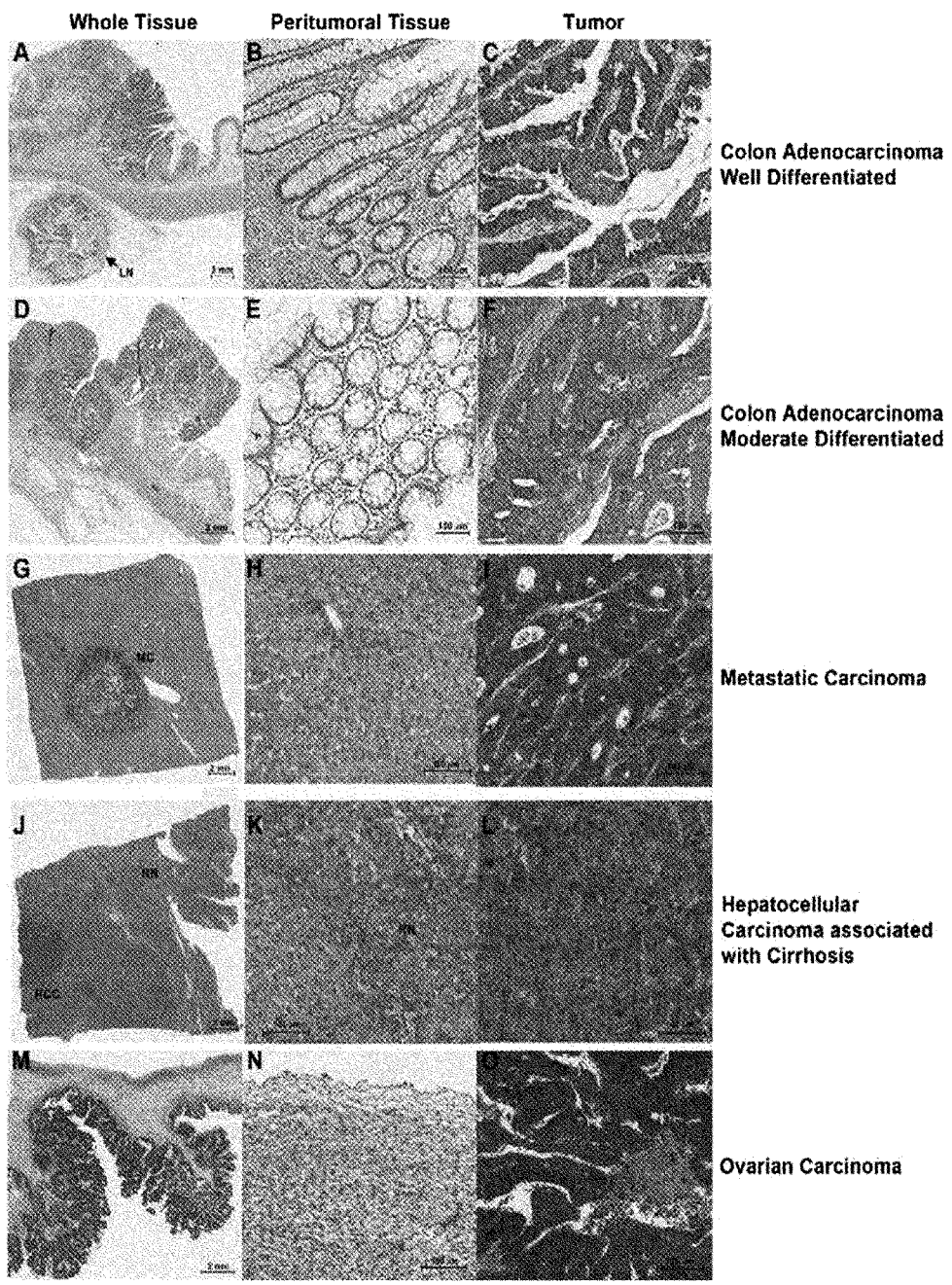
FIG. 6 shows results of an immunohistochemical assay for eIF3m in human tissues.

Confirmation of the Preferential Expression of eIF3m in Human Colon Carcinoma Tissues The expression of eIF3m was also detected as measured by qRT-PCR and Western blotting. To examine whether eIF3m is expressed only in particular cells of tissues, immunohistochemistry (IHC) was performed on tissue sections. A primary antibody for use in Western blotting was applied to well-differentiated lymph nodal metastatic colorectal adenocarcinoma cells and moderately differentiated colorectal adenocarcinoma cells (FIGS. 6D and 6F). As a result, a remarkably high expression level of eIF3m was detected in cells within tumor regions (FIGS. 6C and 6F) and in the metastatic carcinoma cells in regional lymph node (LN) (FIG. 6A). In contrast, low signals were detected in non-neoplastic epithelial cells of peritumoral tissues which are located in the lining lumen of the colon where cellular regeneration occurs constantly (FIGS. 6B and 6E). The subcellular localization of eIF3m expression was confirmed at higher magnification. eIF3m expression was not detected in the blue counterstained nuclei but was confined to the cytosol in both carcinoma and non-neoplastic epithelial cells. Compared to epithelial cells in crypt regions, the matrix cells present therebetween had lower expression levels. No eIF3m was observed in the muscular cells (FIGS. 6A and 6D). A high expression level of eIF3m was observed in metastatic carcinoma on hepatic tissues (FIGS. 6G to 6I). Whereas peritumoral tissues were relatively clear, metastatic regions showed a strong expression of eIF3m in a pattern similar to that in tumors of colorectal adenocarcinoma, as shown in FIG. 6G and 6F. A high eIF3m expression level was also detected in hepatocellular carcinoma (FIGS. 6J and 6L). RN (regenerating nodules) in cirrhosis regions characterized by responsive proliferation also showed strong expression of eIF3m, compared to peripheral region of normal tissues. Similarly, serous cystadnocarcinoma showed high expression levels of eIF3m than did peritumoral regions of the ovarian tissues (FIGS. 6M and 6O).

These results suggest that eIF3m is highly expressed in tumor and peritumoral tissues where cell proliferation is active at higher level.

Silencing eIF3m Expression Reduces Proliferation of Human Colon Cancer Cells

Figure 9:
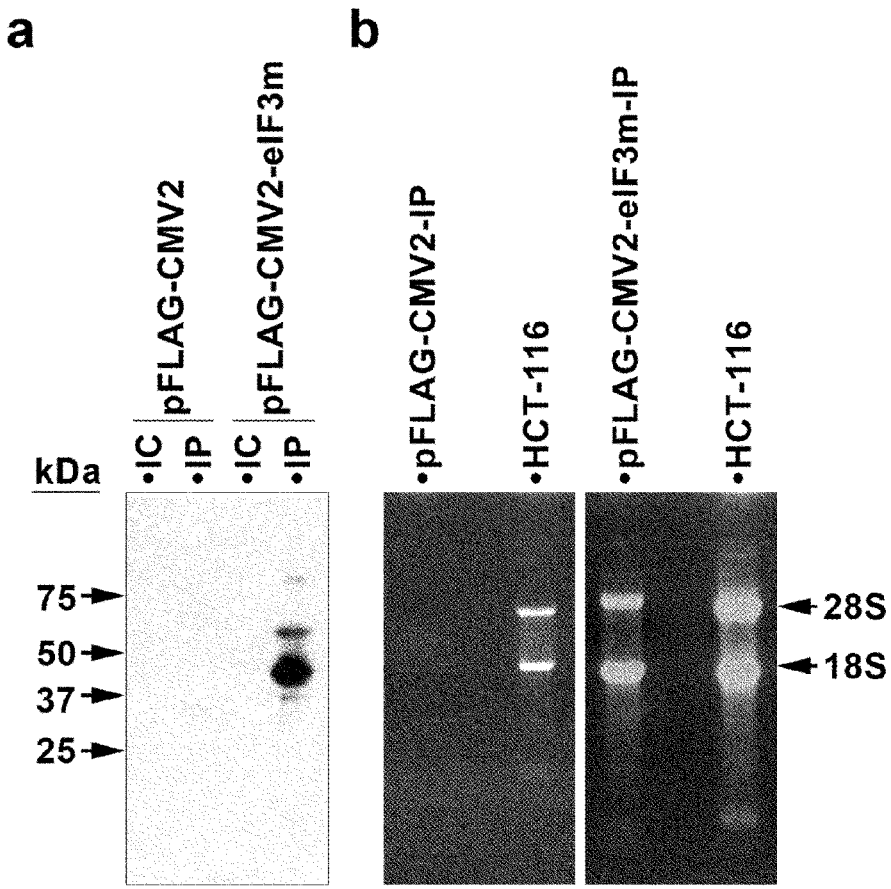
FIG. 9 shows eIF3m and RNA in immunoprecipitate of HCT-116 cells. (a) Western blot of eIF3m from the immunoprecipitated cell lysate. Blank vector control(pFLAG-CMV2) did not show any detectable band in either input control(IC) or in immunoprecipitate of anti-FLAG antibody conjugated affinity gel (IP). However, in IP of pFLAG-CMV2-eIF3m transfected HCT-116 cells the band appeared with designated size. (b) The RNA resolved on formaldehyde gel after extraction from the immunoprecipitate. The blank vector control did not give RNA, but in pFLAG-CMV2-eIF3m transfected cells appeared RNA.
Figure 10:
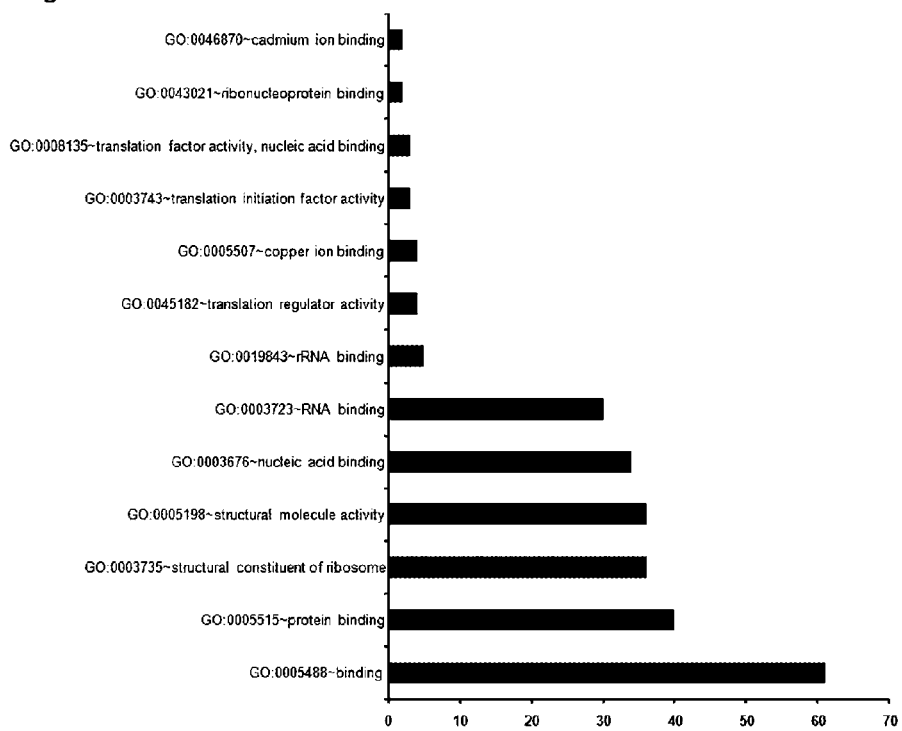
FIG. 10 shows oncological analysis results of related molecules.
Figure 11:
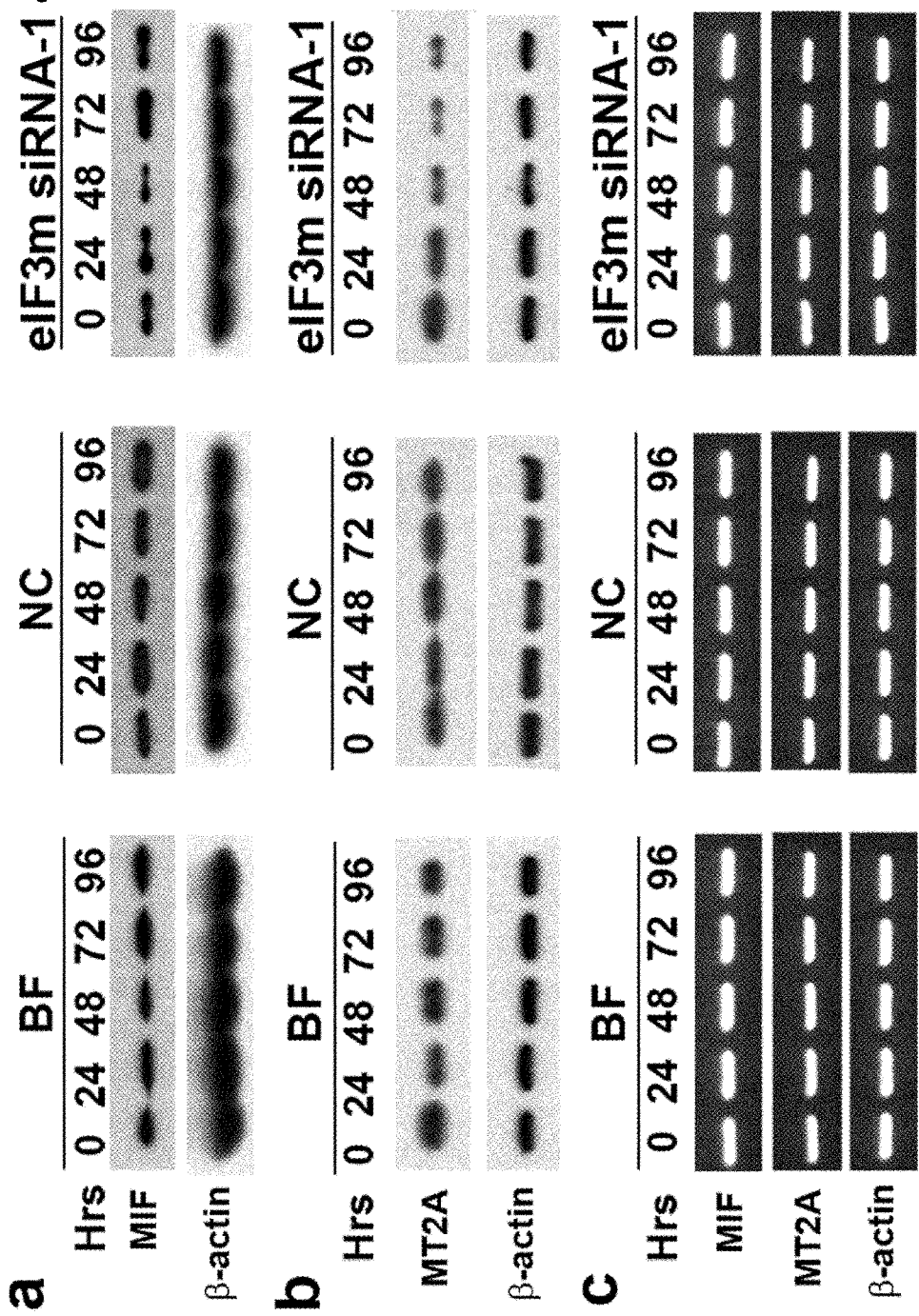
FIG. 11 shows the protein expression of macrophage migration inhibitory factor (MIF) (a) and metallothione in 2A (MT2A) (b) in HCT-116 cells at 0,24, 48, 72 and 96 hrs after eIF3m siRNA-1 transfection detected by Westernblot. Human beta-actin was also detected for the loading control. (c) Transcript level of MIF and MT2A detected by RT-PCR in HCT-116 cells at 0, 24, 48, 72 and 96 hrs after eIF3m siRNA-1 transfection.
Figure 12:
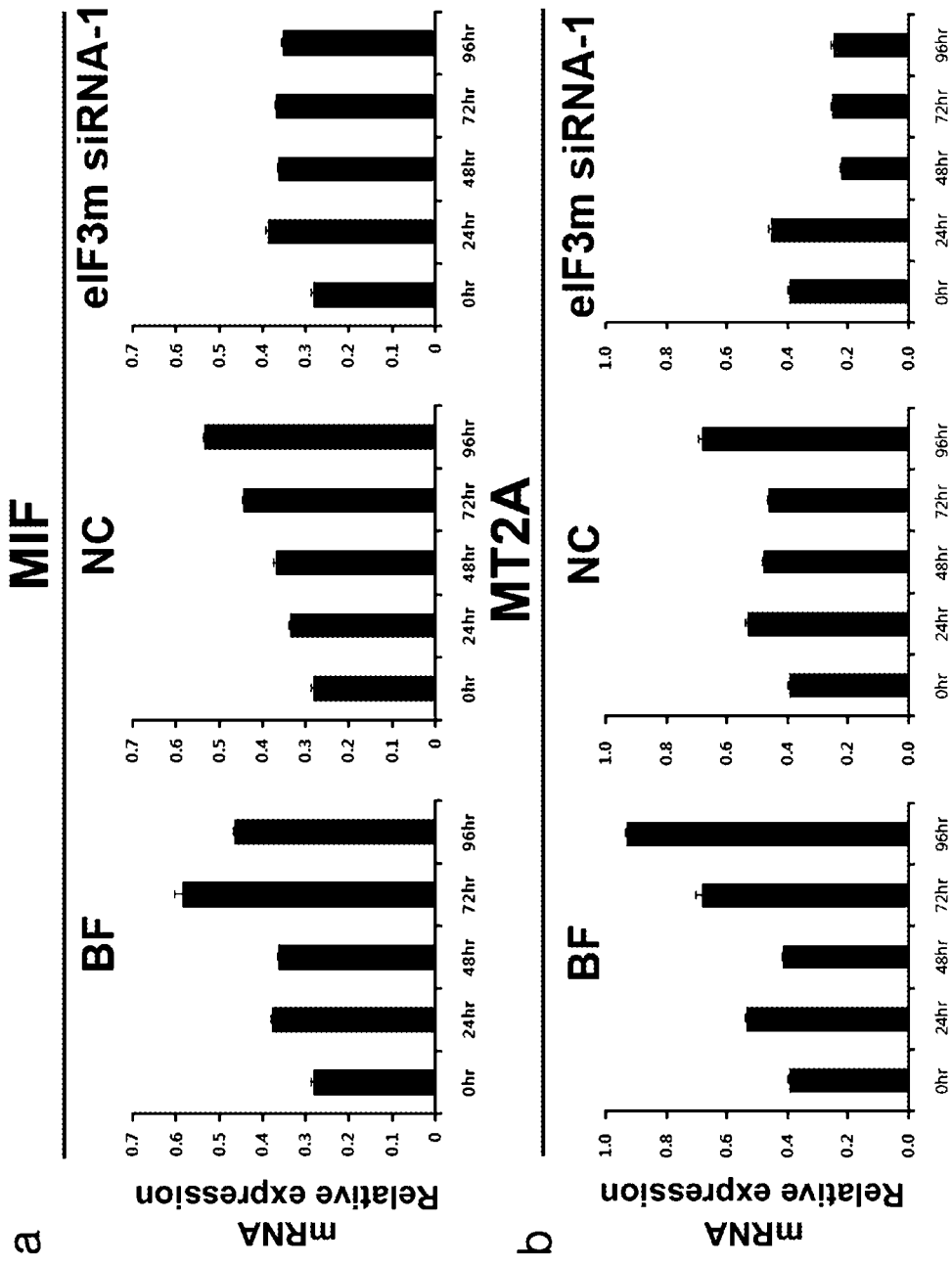
FIG. 12 shows the specificity of reaction confirmed by sequencing of PCR product.mRNA levels of MIF (a) and MT2A (b) as measured by qRT-PCR (relative quantification by normalized with beta-actin mRNA expression) in HCT-116 cells at various times after eIF3m siRNA-1 transfection.

The low expression of eIF3m in the peritumoral regions confirmed by IHC, suggests that eIF3m is also involved in reactive proliferation as well as in tumor progression. To determine the effect of eIF3m expression on cell proliferation, we studied the effect of silencing eIF3m mRNA in HCT-116 colon cancer cells using siRNA. First, we transfected HCT-116 colon cancer cells with buffer (BF), non-human negative control siRNA (NC), and eIF3m specific siRNA-1/-3. Then we examined the expression of eIF3m every 24 hours for 96 hrs after transfection by Western blotting (FIGS. 7A and 8A). eIF3m expression was reduced from 24 hrs after siRNA transfection until 96 hrs. In contrast, BF or NC did not change the level of eIF3m protein. The confluency after BF and NC rapidly increased and reached a plateau at 72 hrs (FIG. 7B), but eIF3m siRNA-1 slowed down the proliferation from 24 hrs. The confluency at 96 hrs of eIF3m siRNA was lower than that with BF or NC (FIG. 7B). MTT assays confirmed this by showing no more increase than 3 fold with eIF3m siRNA at 72 hrs compared to 6 fold with NC and 5 fold with BF (FIG. 7C). This result was confirmed again by using another siRNA, siRNA-3 (FIG. 8B). Silencing efficacies of siRNA-1 and -3 compared to NC at 96 hrs were 46.4% (Student's t-test p=1.3×10$^{-5}$) and 65.3% (Student's t-test p=2.8× 10$^{-9}$), respectively. These results suggest that proliferation of cancer cells is retarded by silencing eIF3m expression.

eIF3m-Associated Transcript eIF3m is known as one of the "non-core" eIF3 subunits. Putative eIF3m is one of the components of the 40S ribosomal subunit and can be involved in the expression of a subset of transcripts in association with cell proliferation depending on physiological state of the cell. Thus, the present inventors employed a ribonomics strategy to find transcripts which were expressed at a high level in association with eIF3m. eIF3m was cloned into a FLAG tagging expression plasmid and expressed under the control of CMV2 promoter in HCT-116 colon cancer cell lines. After 48 hours of transfection, the cultured cells were harvested and the lysate was immunoprecipitated with FLAG-M2 affinity gel. The eIF3m-inserted plasmid generated a designated size of eIF3m band on Western blots, but the blank vector control did not (FIG. 9A). Total RNA was extracted from the immunoprecipitated gel pellet. The eIF3m expression clone generated a detectable amount of RNA in the immunoprecipitate but a blank vector did not (FIG. 9B). This RNA was used to make a cDNA library. Among the 344 randomly picked clones, sequences of 181 clones were successfully read and 81 representative kinds of eIF3m-associated genes are given in Table 2, below. These sequences include 75 ribosomal protein genes (41.4%), eIF3m itself (25.4%), 54 representative single genes (29.8%), and 8 unclassified entries (4.4%). Classification of these genes by gene ontology for molecular function revealed that most of the eIF3m-associated transcripts encode genes for protein translation (protein binding, structural constituent of ribosome, translation initiation factor activity, and ribonucleoprotein binding) and RNA binding (nucleic acid binding, RNA binding, and rRNA binding) (Table 2). Another notable class of genes was concerned with metal ion binding activity (cadmium ion and copper ion binding). For an advanced study on these transcripts, a choice was made of macrophage migration inhibitory factor (MIF)gene. When eIF3m siRNA-treated HCT-116 cell lysate was examined by Western blot, the protein level of MIF decreased until 48 hours as was eIF3m expression but it revived to normal level from 72 hrs (FIG. 11A). UCIMT antibody detects both MT1 and MT2 isoforms, but MT2A was major form in ribonomics, so we applied the antibody to detect MT2A protein. The protein level of MT2A also decreased until 48 hrs, but did not return back to normal level (FIG. 11B) unlike MIF. However, mRNA level did not correlate with protein level but showed minor change in different way (FIGS. 11A, 11B and 11C)). This suggests that eIF3m influence on the expression of a designated subset of cell proliferation genes by modulating translation efficiency or affecting stability of target mRNA.

Figure 13:
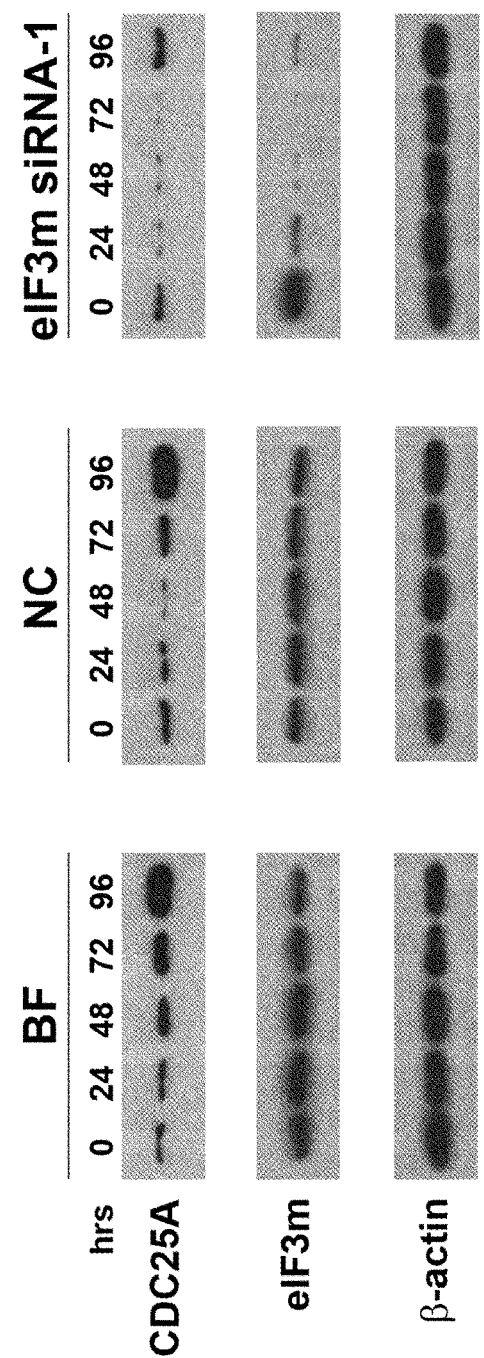
FIG. 13 shows the regulated expression of cell division cycle 25 homolog A (CDC25A) protein in HCT-116 cells at 0, 24, 48, 72 and 96 hrs after eIF3m siRNA-1 transfection. Human beta-actin was also detected for the loading control.

Also, the protein level of MIF and MT2A was examined for whether it is influenced by eIF3m expression in the HCT-116 cells. Since, Lim et al. (2009) reported cell division cycle 25 homolog A (CDC25A) degradation and G1-arrest by MT2A silencing in breast cancer cells, whether eIF3m silencing affects CDC25A level was checked and it was immediately found that it decreased CDC25A from 24 hrs until 72 hrs (FIG. 13). These results confirm eIF3m expression influence on cell cycle regulation.

Table 2

| Gene Description | Gene Symbol | Possible Molecular Function[1] | RefSeq ID |
|---|---|---|---|
| ADAPTOR-RELATED PROTEIN COMPLEX 4, SIGMA 1 SUBUNIT | AP4S1 | Protein transporter activity | NM_007077 |
| ATX1 ANTIOXIDANT PROTEIN 1 HOMOLOG (YEAST) | ATOX1 | Copper-chaperone activity | NM_004045 |
| ATP SYNTHASE, H + TRANSPORTING, MITOCHONDRIAL F0 COMPLEX, SUBUNIT C1 (SUBUNIT 9) | ATP5G1 | Transporter activity | NM_005175 |
| ATP SYNTHASE, H + TRANSPORTING, MITOCHONDRIAL F0 COMPLEX, SUBUNIT G | ATP5L | ATPase activity | NM_006476 |
| BETA-2-MICROGLOBULIN | B2M | Structural molecular activity | NM_004048 |
| SIMILAR TO RPE-SPONDIN | C20ORF199 | N/A[2] | XM_945311 |
| CHROMOSOME 21 OPEN READING FRAME 45 | C21ORF45 | N/A | NM_018944 |
| CHROMOSOME 7 OPEN READING FRAME 30 | C7ORF30 | N/A | NM_138446 |
| HYPOTHETICAL PROTEIN FLJ10803 | C7ORF44 | N/A | NM_018224 |
| COILED-COIL DOMAIN CONTAINING 72 | CCDC72 | N/A | NM_015933 |
| EUKARYOTIC TRANSLATION INITIATION FACTOR 1 | EIF1 | Translation initiation factor activity | NM_005801 |
| EUKARYOTIC TRANSLATION INITIATION FACTOR 2, SUBUNIT 2 BETA, 38KDA | EIF2S2 | Translation initiation factor activity | NM_003908 |

| Gene Description | Gene Symbol | Possible Molecular Function[1] | RefSeq ID |
| --- | --- | --- | --- |
| DENDRITIC CELL PROTEIN | EIF3M | Translation initiation factor activity | NM_006360 |
| ENHANCER OF YELLOW 2 HOMOLOG (DROSOPHILA) | ENY2 | Nucleic acid binding activity | NM_020189 |
| FAMILY WITH SEQUENCE SIMILARITY 49, MEMBER B | FAM49B | N/A | NM_016623 |
| FXYD DOMAIN CONTAINING ION TRANSPORT REGULATOR 5 | FXYD5 | Cadherin binding | NM_014164 |
| CHORIONIC SOMATOMAMMOTROPIN HORMONE 1 (PLACENTAL LACTOGEN) | GH1 | Growth hormone receptor binding | NM_022644 |
| HIGH-MOBILITY GROUP NUCLEOSOME BINDING DOMAIN 1 | HMGN1 | DNA binding | NM_004965 |
| HEMATOLOGICAL AND NEUROLOGICAL EXPRESSED 1 | HN1 | N/A | NM_016185 |
| MACROPHAGE MIGRATION INHIBITORY FACTOR (GLYCOSYLATION-INHIBITING FACTOR) | MIF | Cytokine, phenylpyruvate tautomerase activity | NM_002415 |
| METALLOTHIONEIN 1E (FUNCTIONAL) | MT1E | Metal ion binding | NM_175617 |
| METALLOTHIONEIN 1X | MT1X | Metal ion binding | NM_005952 |
| METALLOTHIONEIN 2A | MT2A | Metal ion binding | NM_005953 |
| RIBOSOMAL PROTEIN S13 | RPS13 | Structural constituent of ribosome | NM_001017 |
| RIBOSOMAL PROTEIN S14 | RPS14 | Structural constituent of ribosome | NM_001025071 |
| RIBOSOMAL PROTEIN S15 | RPS15 | Structural constituent of ribosome | NM_001018 |
| RIBOSOMAL PROTEIN S15A | RPS15A | Structural constituent of ribosome | NM_001019 |
| RIBOSOMAL PROTEIN S17 | RPS17 | Structural constituent of ribosome | NM_001021 |
| RIBOSOMAL PROTEIN S21 | RPS21 | Structural constituent of ribosome | NM_001024 |
| RIBOSOMAL PROTEIN S23 | RPS23 | Structural constituent of ribosome | NM_001025 |
| RIBOSOMAL PROTEIN S25 | RPS25 | Structural constituent of ribosome | NM_001028 |
| RIBOSOMAL PROTEIN S27 (METALLOPANSTIMULIN 1) | RPS27 | Structural constituent of ribosome | NM_001030 |
| RIBOSOMAL PROTEIN S28 | RPS28 | Structural constituent of ribosome | NM_001031 |
| RIBOSOMAL PROTEIN S29 | RPS29 | Structural constituent of ribosome | NM_001030001 |
| RIBOSOMAL PROTEIN S4, X-LINKED | RPS4X | Structural constituent of ribosome | NM_001007 |
| RIBOSOMAL PROTEIN S8 | RPS8 | Structural constituent of ribosome | NM_001012 |
| S100 CALCIUM BINDING PROTEIN A6 (CALCYCLIN) | S100A6 | Growth factor activity | NM_014624 |
| SEC61 BETA SUBUNIT | SEC61B | P-P-bond-hydrolysis-driven protein transmembrane transporter activity | NM_006808 |
| SMALL EDRK-RICH FACTOR 2 | SERF2 | N/A | NM_016400 |
| SERPIN PEPTIDASE INHIBITOR, CLADE B (OVALBUMIN), MEMBER 6 | SERPINB6 | Serine-type endopeptidase inhibitor activity | NM_004568 |
| SMALL NUCLEAR RIBONUCLEOPROTEIN D2 POLYPEPTIDE 16.5 KDA | SNRPD2 | Protein binding | NM_004597 |
| SMALL NUCLEAR RIBONUCLEOPROTEIN POLYPEPTIDE G | SNRPG | Protein binding | NM_003096 |
| TRANSLOCASE OF INNER MITOCHONDRIAL MEMBRANE 50 HOMOLOG (YEAST) | TIMM50 | Protein tyrosine phosphatase activity; Ribonucleoprotein binding; Protein serine/threonine phosphatase activity | NM_001001563 |
| TRANSMEMBRANE PROTEIN 14C | TMEM14C | N/A | NM_016462 |
| TUMOR PROTEIN, TRANSLATIONALLY-CONTROLLED 1 | TPT1 | Calcium ion binding | NM_003295 |
| TRIO AND F-ACTIN BINDING PROTEIN | TRIOBP | Actin binding; GTP-Rho binding | NM_138632 |
| UBIQUITIN A-52 RESIDUE RIBOSOMAL PROTEIN FUSION PRODUCT 1 | UBA52 | Structural constituent of ribosome | NM_001033930 |
| UBIQUITIN-CONJUGATING ENZYME E2L 3 | UBE2L3 | Ubiquitin-protein ligase activity | NM_198157 |
| VACUOLAR PROTEIN SORTING 35 (YEAST) | VPS35 | Ubiquitin binding;Transcrition corepressor acotivity | NM_018206 |
| ZONA PELLUCIDA GLYCOPROTEIN 2 (SPERM RECEPTOR) | ZP2 | Coreceptor activity | NM_003460 |
| NADH DEHYDROGENASE (UBIQUINONE) 1 ALPHA SUBCOMPLEX, 4, 9KDA | NDUFA4 | NADH dehydrogenase activity | NM_002489 |
| PEROXIREDOXIN 1 | PRDX1 | Peroxiredoxin activity | NM_002574 |
| PITUITARY TUMOR-TRANSFORMING 1 | PTTG1 | Transcription factor activity | NM_004219 |
| RIBOSOMAL PROTEIN L10 | RPL10 | Structural constituent of ribosome | NM_006013 |
| RIBOSOMAL PROTEIN L13 | RPL13 | Structural constituent of ribosome | NM_033251 |
| RIBOSOMAL PROTEIN L17 | RPL17 | Structural constituent of ribosome | NM_001035005 |
| RIBOSOMAL PROTEIN L21 | RPL21 | Structural constituent of ribosome | NM_000982 |
| RIBOSOMAL PROTEIN L23 | RPL23 | Structural constituent of ribosome | NM_000978 |
| RIBOSOMAL PROTEIN L23A | RPL23A | Structural constituent of ribosome | NM_000984 |
| RIBOSOMAL PROTEIN L27 | RPL27 | Structural constituent of ribosome | NM_000988 |
| RIBOSOMAL PROTEIN L27A | RPL27A | Structural constituent of ribosome | NM_000990 |
| RIBOSOMAL PROTEIN L28 | RPL28 | Structural constituent of ribosome | NM_000991 |
| RIBOSOMAL PROTEIN L30 | RPL30 | Structural constituent of ribosome | NM_000989 |
| RIBOSOMAL PROTEIN L31 | RPL31 | Structural constituent of ribosome | NM_000993 |
| RIBOSOMAL PROTEIN L32 | RPL32 | Structural constituent of ribosome | NM_000994 |
| RIBOSOMAL PROTEIN L35A | RPL35A | Structural constituent of ribosome | NM_000996 |
| RIBOSOMAL PROTEIN L36 | RPL36 | Structural constituent of ribosome | NM_033643 |

| Gene Description | Gene Symbol | Possible Molecular Function[1] | RefSeq ID |
|---|---|---|---|
| RIBOSOMAL PROTEIN L37 | RPL37 | Structural constituent of ribosome | NM_000997 |
| RIBOSOMAL PROTEIN L37A | RPL37A | Structural constituent of ribosome | NM_000998 |
| RIBOSOMAL PROTEIN L39 | RPL39 | Structural constituent of ribosome | NM_001000 |
| RIBOSOMAL PROTEIN L41 | RPL41 | Structural constituent of ribosome | NM_021104 |
| RIBOSOMAL PROTEIN L5 | RPL5 | Structural constituent of ribosome | NM_000969 |
| RIBOSOMAL PROTEIN L6 | RPL6 | Structural constituent of ribosome | NM_001024662 |
| RIBOSOMAL PROTEIN L7A | RPL7A | Structural constituent of ribosome | NM_000972 |
| RIBOSOMAL PROTEIN S11 | RPS11 | Structural constituent of ribosome | NM_001015 |

Effect of eIF3m Silencing on Cell Cycle

Figure 14:
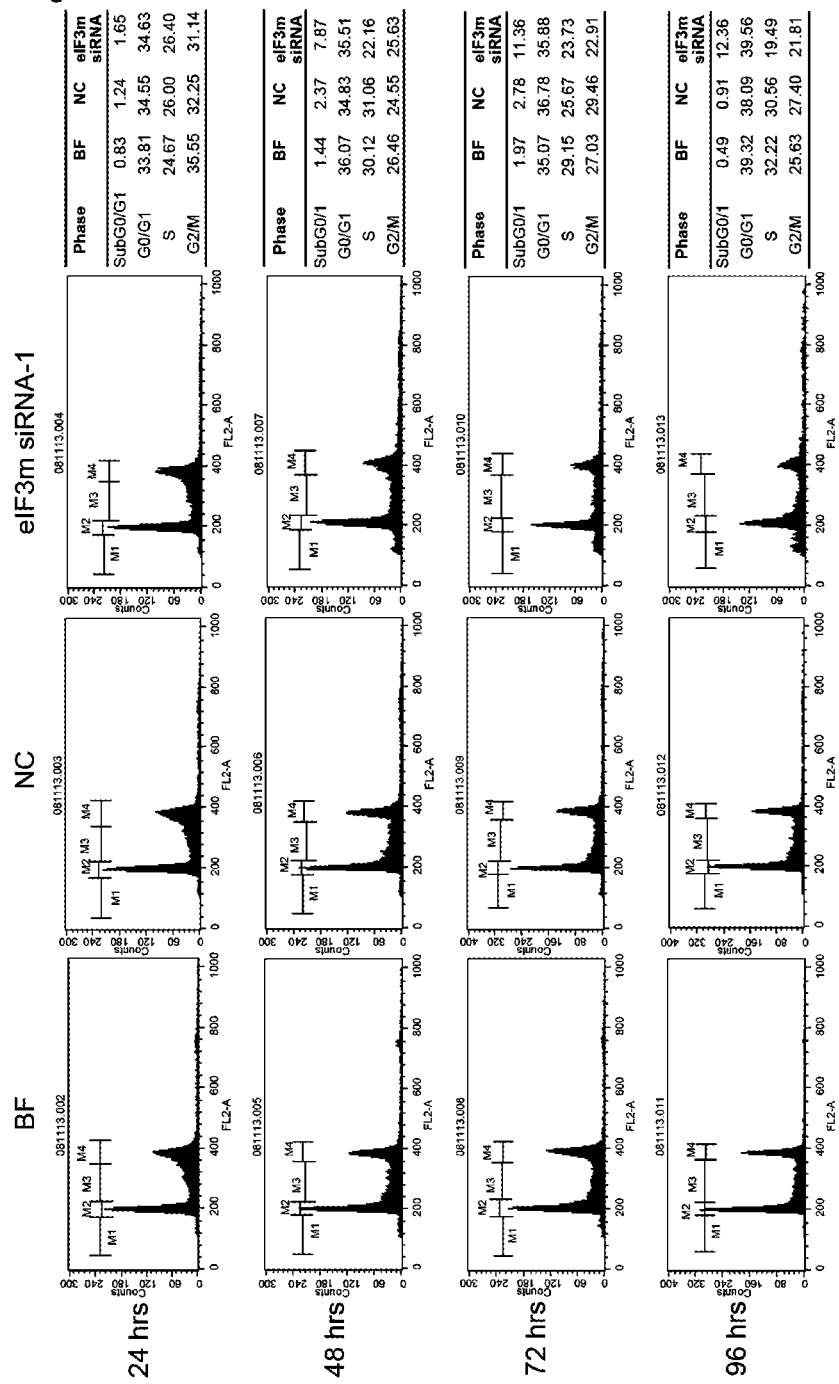
FIG. 14 shows that Sub-G0/G1 population of HCT-116 colon cancer cell line increases when eIF3m expression is silenced. The nuclear contents of siRNA transfected cells were measured every 24 hours after treatment by flow cytometry to see the cell cycle progression. BF and NC controls did not show any significant cell cycle differences among mitotic cellcycle stages. The eIF3m siRNA-1 treatment increased sub-G0/G1 stage at 24 hours, and remained elevated until 96 hours.
Figure 15:
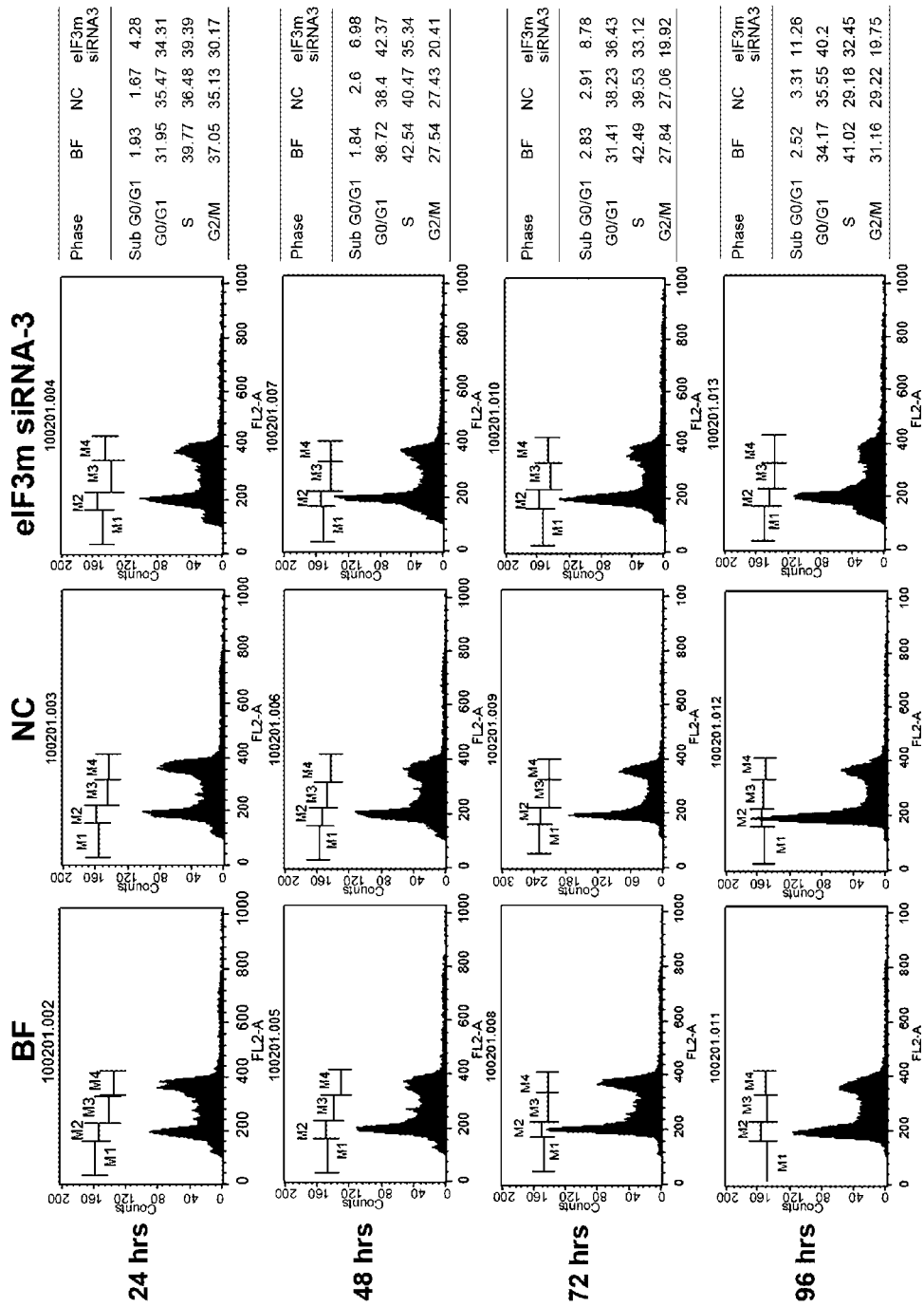
FIG. 15 shows that the nuclear contents of siRNA transfected cells were measured every 24 hours after treatment, by flow cytometry to see the cell cycle progression. There were no significant differences in sub G0/G1 phase in BF and NC controls through the culture period, but sub-G0/G1 stage after eIF3m siRNA-3 treatment was elevated until 96 hours.

Cell proliferation or cell death is closely associated with cell differentiation since a continuous cell cycle is the first entrance of determining both proliferation and apoptosis. Hence, in the context of the cell proliferation retardation, as shown in FIG. 7, by eIF3m silencing, the cell cycle progression following eIF3m knockdown in HCT-116 cell lines was analyzed using flow cytometry. The HCT-116 cells were treated with eIF3m siRNA, BF, or NC controls. After 24 hrs of siRNA transfection, there was no significant difference in the proportion of each mitosis stage between groups treated with NC, BF, and eIF3m siRNA (FIGS. 14 and 15). As the time point moves from 24 hrs to 48 hrs, the portion of sub-G0/G1 phase in eIF3m siRNA-treated cells increased from 1.65% to 7.87%, but sub-G0/G1 of BF and NC remained at 1.44% and 2.37%, respectively. Interestingly, the proportion of S phase of eIF3m siRNA-1 treated cells decreased to 22.16% from 26.40% while it increased from 24.67% to 30.12% and from 26.00% to 31.06%, respectively in BF and NC. When the cells were cultured for 72 hrs, the increment of sub-G0/G1 portion of eIF3m siRNA-1 (11.36%) became more prominent compared to BF (1.97%) or NC (2.78%). The S phase in the case of eIF3m siRNA-1 at the same time point (23.73%) was still lower than those with BF (29.15%) or NC (25.67%). In addition, the G2/M phase that did not show significant difference at previous time points decreased to 22.91% compared to 27.03% with BF and 29.46% with NC at 72 hrs. This trend was maintained for 96 hrs, sub-G0/G1 phase reaching 12.36% in eIF3m siRNA-1 while remaining low in BF (0.49%) and NC (0.91%). On the other hand, the S phase became much lower in eIF3m siRNA-1 (19.49%) compared to BF (32.22%) and NC (30.56%), and similarly decreased in G2/M phase (21.81%) compared to BF (25.63%) and NC (27.40%). eIF3m siRNA-3 also showed increased sub G0/G1 from 24 hrs and at 96 hrs it showed 11.26% of sub G0/G1 compared to BF (2.52%) or NC (3.31%) and decreased G2/M-phase (19.75%) portion compared to BF (31.16%) or NC (29.22%). Taken together, these results suggest that silencing of eIF3m expression increased sub-G0/G1 proportion and led to cell death. Thus, eIF3m expression seems to be required for the cells to continue cell-cycle and eventually for cell proliferation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for diagnosing a cancer in a subject by detecting an eIF3m polynucleotide wherein the cancer is selected from lung cancer, colon cancer, and rectal cancer, said method comprising:
   (a) providing a tissue specimen or cells from the subject;
   (b) treating the tissue specimen or the cells with an agent that measures an mRNA level of eIF3m, wherein the agent is a pair of primers wherein one primer of the pair consists of the nucleotide sequence set forth in SEQ ID NO:27 and the other primer of the pair consists of the nucleotide sequence set forth in SEQ ID NO:28;
   (c) detecting a binding product of the agent to a polynucleotide complementary thereto; and
   (d) quantitatively comparing the amount of binding product detected in the tissue specimen or the cells from the subject and a normal control, wherein an increase in the level of the eIF3m polynucleotide in the tissue specimen or cells from the subject compared to the control indicates the subject has cancer.

2. A method for diagnosing a cancer in a subject comprising: measuring the level of an eIF3m mRNA in a tissue specimen or cells obtained from the subject, using a kit for diagnosing cancer, comprising an agent for measuring the level of an eIF3m mRNA, wherein the cancer is selected from the group consisting of lung cancer, colon cancer, and rectal cancer, wherein the kit comprises a pair of primers wherein one primer of the pair consists of the nucleotide sequence set forth in SEQ ID NO:27 and the other primer of the pair consists of the nucleotide sequence set forth in SEQ ID NO:28.

* * * * *

UNITED STATES PATENT AND TRADEMARK OFFICE
CERTIFICATE OF CORRECTION

PATENT NO.        : 8,673,573 B2                                              Page 1 of 1
APPLICATION NO.   : 12/997560
DATED             : March 18, 2014
INVENTOR(S)       : Lee et al.

It is certified that error appears in the above-identified patent and that said Letters Patent is hereby corrected as shown below:

In the Claims

Column 31, Line 54, Claim 1:
"an eIF3m polynucleotide wherein the cancer is selected" should read, --an eIF3m polynucleotide wherein the cancer is selected--.

Column 31, Line 59, Claim 1:
"that measures an mRNA level of eIF3m, wherein the" should read, --that measures an mRNA level of eIF3m, wherein the--.

Column 32, Line 53, Claim 1:
"level of the eIF3m polynucleotide in the tissue specimen" should read, --level of the eIF3m polynucleotide in the tissue specimen--.

Column 32, Line 57, Claim 2:
"measuring the level of an eIF3m mRNA in a tissue" should read, --measuring the level of an eIF3m mRNA in a tissue--.

Column 32, Line 60, Claim 2:
"level of an eIF3m mRNA, wherein the cancer is selected from" should read, --level of an eIF3m mRNA, wherein the cancer is selected from--.

Signed and Sealed this
Fourteenth Day of October, 2014

Michelle K. Lee
*Deputy Director of the United States Patent and Trademark Office*